US011399722B2

(12) United States Patent
Al-Ali et al.

(10) Patent No.: US 11,399,722 B2
(45) Date of Patent: Aug. 2, 2022

(54) PLETHYSMOGRAPHIC RESPIRATION RATE DETECTION

(71) Applicant: MASIMO CORPORATION, Irvine, CA (US)

(72) Inventors: Ammar Al-Ali, San Juan Capistrano, CA (US); Anmol Majmudar, Irvine, CA (US)

(73) Assignee: MASIMO CORPORATION, Irvine, CA (US)

( * ) Notice: Subject to any disclaimer, the term of this patent is extended or adjusted under 35 U.S.C. 154(b) by 565 days.

(21) Appl. No.: 16/119,215

(22) Filed: Aug. 31, 2018

(65) Prior Publication Data

US 2019/0076028 A1    Mar. 14, 2019

Related U.S. Application Data

(60) Continuation of application No. 15/095,912, filed on Apr. 11, 2016, now Pat. No. 10,098,550, which is a
(Continued)

(51) Int. Cl.
*A61B 5/0205* (2006.01)
*A61B 5/08* (2006.01)
(Continued)

(52) U.S. Cl.
CPC ........ *A61B 5/0205* (2013.01); *A61B 5/02007* (2013.01); *A61B 5/029* (2013.01);
(Continued)

(58) Field of Classification Search
CPC . A61B 5/14551; A61B 5/0816; A61B 5/0205; A61B 5/7246
See application file for complete search history.

(56) References Cited

U.S. PATENT DOCUMENTS 3,682,161 A    8/1972  Alibert
4,109,643 A    8/1978  Bond et al.
(Continued)

FOREIGN PATENT DOCUMENTS

CA    2262236    4/2008
EP    0716628    12/1998
(Continued)

OTHER PUBLICATIONS

US 8,845,543 B2, 09/2014, Diab et al. (withdrawn)
(Continued)

*Primary Examiner* — Christian Jang
*Assistant Examiner* — Karen E Toth
(74) *Attorney, Agent, or Firm* — Knobbe, Martens, Olson & Bear, LLP

(57) ABSTRACT

A plethysmographic respiration processor is responsive to respiratory effects appearing on a blood volume waveform and the corresponding detected intensity waveform measured with an optical sensor at a blood perfused peripheral tissue site so as to provide a measurement of respiration rate. A preprocessor identifies a windowed pleth corresponding to a physiologically acceptable series of plethysmograph waveform pulses. Multiple processors derive different parameters responsive to particular respiratory effects on the windowed pleth. Decision logic determines a respiration rate based upon at least a portion of these parameters.

16 Claims, 17 Drawing Sheets

Related U.S. Application Data division of application No. 13/076,423, filed on Mar. 30, 2011, now Pat. No. 9,307,928.

(60) Provisional application No. 61/364,141, filed on Jul. 14, 2010, provisional application No. 61/319,256, filed on Mar. 30, 2010.

(51) Int. Cl.

| | |
|---|---|
| *A61B 5/026* | (2006.01) |
| *A61B 5/0295* | (2006.01) |
| *A61B 5/00* | (2006.01) |
| *G16H 15/00* | (2018.01) |
| *G16H 50/30* | (2018.01) |
| *G16H 50/00* | (2018.01) |
| *A61B 5/02* | (2006.01) |
| *A61B 5/029* | (2006.01) |
| *A61B 5/1455* | (2006.01) |

(52) U.S. Cl.
CPC .......... *A61B 5/0261* (2013.01); *A61B 5/0295* (2013.01); *A61B 5/0816* (2013.01); *A61B 5/6826* (2013.01); *A61B 5/7203* (2013.01); *A61B 5/725* (2013.01); *A61B 5/7225* (2013.01); *A61B 5/7228* (2013.01); *A61B 5/7246* (2013.01); *A61B 5/7253* (2013.01); *A61B 5/7264* (2013.01); *A61B 5/7278* (2013.01); *A61B 5/742* (2013.01); *A61B 5/7405* (2013.01); *A61B 5/746* (2013.01); *A61B 5/7475* (2013.01); *G16H 15/00* (2018.01); *G16H 50/00* (2018.01); *G16H 50/30* (2018.01); *A61B 5/08* (2013.01); *A61B 5/0806* (2013.01); *A61B 5/14552* (2013.01)

(56) References Cited

U.S. PATENT DOCUMENTS

| | | |
|---|---|---|
| 4,127,749 A | 11/1978 | Atoji et al. |
| 4,326,143 A | 4/1982 | Guth et al. |
| 4,507,653 A | 3/1985 | Bayer |
| 4,537,200 A | 8/1985 | Widrow |
| 4,685,140 A | 8/1987 | Mount, II |
| 4,714,341 A | 12/1987 | Hamaguri |
| 4,848,901 A | 7/1989 | Hood, Jr. |
| 4,867,165 A | 9/1989 | Noller et al. |
| 4,884,809 A | 12/1989 | Rowan |
| 4,958,638 A | 9/1990 | Sharpe et al. |
| 4,960,128 A | 10/1990 | Gordon et al. |
| 4,964,408 A | 10/1990 | Hink et al. |
| 5,033,032 A | 7/1991 | Houghtaling |
| 5,041,187 A | 8/1991 | Hink et al. |
| 5,069,213 A | 12/1991 | Polczynski |
| 5,111,817 A | 5/1992 | Clark et al. |
| 5,119,814 A | 6/1992 | Minnich |
| 5,143,078 A | 9/1992 | Mather et al. |
| 5,163,438 A | 11/1992 | Gordon et al. |
| 5,273,036 A | 12/1993 | Kronberg et al. |
| 5,277,181 A | 1/1994 | Mendelson et al. |
| 5,309,922 A | 5/1994 | Schechter et al. |
| 5,319,355 A | 6/1994 | Russek |
| 5,337,744 A | 8/1994 | Branigan |
| 5,341,805 A | 8/1994 | Stavridi et al. |
| 5,353,798 A | 10/1994 | Sieben |
| D353,195 S | 12/1994 | Savage et al. |
| D353,196 S | 12/1994 | Savage et al. |
| 5,377,302 A | 12/1994 | Tsiang |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,448,996 A | 9/1995 | Bellin et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,553,615 A | 9/1996 | Carim et al. |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,613,496 A | 3/1997 | Arand et al. |
| 5,632,272 A | 5/1997 | Diab et al. |
| 5,638,403 A | 6/1997 | Birchler et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,191 A | 9/1997 | Gerdt |
| 5,671,914 A | 9/1997 | Kalkhoran et al. |
| 5,685,299 A | 11/1997 | Diab et al. |
| 5,724,983 A | 3/1998 | Selker et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,766,127 A | 6/1998 | Pologe et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,819,007 A | 10/1998 | Elghazzawi |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,862,805 A | 1/1999 | Nitzan |
| 5,865,736 A | 2/1999 | Baker, Jr. et al. |
| 5,890,929 A | 4/1999 | Mills et al. |
| 5,904,654 A | 5/1999 | Wohltmann et al. |
| 5,919,134 A | 7/1999 | Diab |
| 5,928,156 A | 7/1999 | Krumbiegel |
| 5,934,925 A | 8/1999 | Tobler et al. |
| 5,940,182 A | 8/1999 | Lepper, Jr. et al. |
| 5,984,893 A | 11/1999 | Ward |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,029,665 A | 2/2000 | Berthon-Jones |
| 6,036,642 A | 3/2000 | Diab et al. |
| 6,040,578 A | 3/2000 | Malin et al. |
| 6,045,509 A | 4/2000 | Caro et al. |
| 6,064,910 A | 5/2000 | Andersson et al. |
| 6,066,204 A | 5/2000 | Haven |
| 6,067,462 A | 5/2000 | Diab et al. |
| 6,081,735 A | 6/2000 | Diab et al. |
| 6,083,172 A | 7/2000 | Baker et al. |
| 6,088,607 A | 7/2000 | Diab et al. |
| 6,091,973 A | 7/2000 | Colla et al. |
| 6,110,522 A | 8/2000 | Lepper, Jr. et al. |
| 6,112,171 A | 8/2000 | Sugiyama et al. |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,138,675 A | 10/2000 | Berthon-Jones |
| 6,139,505 A | 10/2000 | Murphy |
| 6,144,868 A | 11/2000 | Parker |

(56) References Cited

U.S. PATENT DOCUMENTS

| | | |
|---|---|---|
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,165,151 A | 12/2000 | Weiner |
| 6,168,568 B1 | 1/2001 | Gavriely |
| 6,178,343 B1 | 1/2001 | Bindszus et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,248,083 B1 | 6/2001 | Smith et al. |
| 6,253,097 B1 | 6/2001 | Aronow et al. |
| 6,254,551 B1 | 7/2001 | Varis |
| 6,255,708 B1 | 7/2001 | Sudharsanan et al. |
| 6,256,523 B1 | 7/2001 | Diab et al. |
| 6,261,238 B1 | 7/2001 | Gavriely |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,331,162 B1 | 12/2001 | Mitchell |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,361,501 B1 | 3/2002 | Amano et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,383,143 B1 | 5/2002 | Rost |
| 6,385,471 B1 | 5/2002 | Mortz |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,443,907 B1 | 9/2002 | Mansy et al. |
| 6,463,311 B1 | 10/2002 | Diab |
| 6,470,199 B1 | 10/2002 | Kopotic et al. |
| 6,486,588 B2 | 11/2002 | Doron et al. |
| 6,487,429 B2 | 11/2002 | Hockersmith et al. |
| 6,491,647 B1 | 12/2002 | Bridger et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,517,497 B2 | 2/2003 | Rymut et al. |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,647,280 B2 | 11/2003 | Bahr et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,659,960 B2 | 12/2003 | Derksen et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,709,402 B2 | 3/2004 | Dekker |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,074 B1 | 4/2004 | Kastle |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,754,516 B2 | 6/2004 | Mannheimer |
| 6,760,607 B2 | 7/2004 | Al-Ali |
| 6,766,038 B1 | 7/2004 | Sakuma et al. |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,839,581 B1 | 1/2005 | El-Solh et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,869,402 B2 | 3/2005 | Arnold |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| 7,096,060 B2 | 8/2006 | Arand et al. |
| D529,616 S | 10/2006 | Deros et al. |

(56) References Cited

U.S. PATENT DOCUMENTS

| | | |
|---|---|---|
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,194,306 B1 | 3/2007 | Turcott |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,267,652 B2 | 9/2007 | Coyle et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,361,146 B1 | 4/2008 | Bharmi et al. |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,398,115 B2 | 7/2008 | Lynn |
| 7,403,806 B2 | 7/2008 | Norris |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,539,533 B2 | 5/2009 | Tran |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,690,378 B1 | 4/2010 | Turcott |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |

(56) References Cited

U.S. PATENT DOCUMENTS

| | | |
|---|---|---|
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,478,538 B2 | 7/2013 | McGonigle et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,584,345 B2 | 10/2013 | Al-Ali et al. |
| 8,577,431 B2 | 11/2013 | Lamego et al. |
| 8,581,732 B2 | 11/2013 | Al-Ali et al. |
| 8,588,880 B2 | 11/2013 | Abdul-Hafiz et al. |
| 8,597,274 B2 | 12/2013 | Sloan |
| 8,600,467 B2 | 12/2013 | Al-Ali et al. |
| 8,606,342 B2 | 12/2013 | Diab |
| 8,622,902 B2 | 1/2014 | Woehrle |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,792,949 B2 | 7/2014 | Baker |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |

(56) References Cited

U.S. PATENT DOCUMENTS

| | | |
|---|---|---|
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,135,398 B2 | 9/2015 | Kaib |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,220,440 B2 | 12/2015 | Addison et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 1/2016 | Abdul-Hafiz et al. |
| 9,267,572 B2 | 2/2016 | Barker et al. |
| 9,277,880 B2 | 2/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,378,637 B2 | 6/2016 | Kaib |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,649,054 B2 | 5/2017 | Lamego et al. |
| 9,659,475 B2 | 5/2017 | Kaib |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| 9,968,266 B2 | 5/2018 | An et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |

(56) References Cited

U.S. PATENT DOCUMENTS

| | | |
|---|---|---|
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| D916,135 S | 4/2021 | Indorf et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| 2001/0002206 A1 | 5/2001 | Diab et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2002/0193670 A1 | 12/2002 | Garfield et al. |
| 2003/0013975 A1 | 1/2003 | Kiani |
| 2003/0015368 A1 | 1/2003 | Cybulski et al. |
| 2003/0018243 A1 | 1/2003 | Gerhardt et al. |
| 2003/0065269 A1 | 4/2003 | Vetter |
| 2003/0076494 A1 | 4/2003 | Bonin et al. |
| 2003/0144582 A1 | 7/2003 | Cohen et al. |
| 2003/0156288 A1 | 8/2003 | Barnum et al. |
| 2003/0158466 A1 | 8/2003 | Lynn et al. |
| 2003/0163033 A1 | 8/2003 | Dekker et al. |
| 2003/0163054 A1 | 8/2003 | Dekker |
| 2003/0212312 A1 | 11/2003 | Coffin, IV et al. |
| 2004/0010202 A1 | 1/2004 | Nakatani |
| 2004/0034293 A1 | 2/2004 | Kimball |
| 2004/0039273 A1 | 2/2004 | Terry |
| 2004/0059203 A1 | 3/2004 | Guerrero |
| 2004/0060362 A1 | 4/2004 | Kjellmann et al. |
| 2004/0087846 A1 | 5/2004 | Wasserman |
| 2004/0106163 A1 | 6/2004 | Workman, Jr. et al. |
| 2004/0133087 A1 | 7/2004 | Ali et al. |
| 2004/0158162 A1 | 8/2004 | Narimatsu |
| 2004/0225332 A1 | 11/2004 | Gebhardt |
| 2004/0260186 A1 | 12/2004 | Dekker |
| 2005/0010166 A1 | 1/2005 | Hickle |
| 2005/0027205 A1 | 2/2005 | Tarassenko et al. |
| 2005/0048456 A1 | 3/2005 | Chefd'hotel et al. |
| 2005/0055276 A1 | 3/2005 | Kiani et al. |
| 2005/0070774 A1 | 3/2005 | Addison et al. |
| 2005/0107699 A1 | 5/2005 | Loftman |
| 2005/0116820 A1 | 6/2005 | Goldreich |
| 2005/0177096 A1 | 8/2005 | Bollish et al. |
| 2005/0199056 A1 | 9/2005 | Strong |
| 2005/0234317 A1 | 10/2005 | Kiani |
| 2006/0047215 A1 | 3/2006 | Newman et al. |
| 2006/0073719 A1 | 4/2006 | Kiani |
| 2006/0129216 A1 | 6/2006 | Hastings et al. |
| 2006/0149144 A1 | 7/2006 | Lynn et al. |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0189871 A1 | 8/2006 | Al-Ali et al. |
| 2006/0189880 A1 | 8/2006 | Lynn et al. |
| 2006/0195041 A1 | 8/2006 | Lynn et al. |
| 2006/0235324 A1 | 10/2006 | Lynn |
| 2006/0238333 A1 | 10/2006 | Welch et al. |
| 2006/0241510 A1 | 10/2006 | Halperin et al. |
| 2006/0258921 A1 | 11/2006 | Addison et al. |
| 2007/0032732 A1 | 2/2007 | Shelley et al. |
| 2007/0055198 A1 | 3/2007 | O'Mahony et al. |
| 2007/0073116 A1 | 3/2007 | Kiani et al. |
| 2007/0093721 A1 | 4/2007 | Lynn et al. |
| 2007/0129643 A1 | 6/2007 | Kwok et al. |
| 2007/0129647 A1 | 6/2007 | Lynn |
| 2007/0135725 A1 | 6/2007 | Hatlestad |
| 2007/0149860 A1 | 6/2007 | Lynn et al. |
| 2007/0163353 A1 | 7/2007 | Lee et al. |
| 2007/0180140 A1 | 8/2007 | Welch et al. |
| 2007/0185397 A1 | 8/2007 | Govari et al. |
| 2007/0213619 A1 | 9/2007 | Linder |
| 2007/0239057 A1 | 10/2007 | Pu et al. |
| 2007/0244377 A1 | 10/2007 | Cozad et al. |
| 2007/0282212 A1 | 12/2007 | Sierra et al. |
| 2008/0013747 A1 | 1/2008 | Tran |
| 2008/0039735 A1 | 2/2008 | Hickerson |
| 2008/0064965 A1 | 3/2008 | Jay et al. |
| 2008/0067132 A1 | 3/2008 | Ross et al. |
| 2008/0071185 A1 | 3/2008 | Beck et al. |
| 2008/0076972 A1 | 3/2008 | Dorogusker et al. |
| 2008/0079299 A1 | 4/2008 | Jackson |
| 2008/0094228 A1 | 4/2008 | Welch et al. |
| 2008/0119716 A1 | 5/2008 | Boric-Lubecke et al. |
| 2008/0161878 A1 | 7/2008 | Tehrani et al. |
| 2008/0167541 A1 | 7/2008 | Takala et al. |
| 2008/0177195 A1 | 7/2008 | Armitstead |
| 2008/0188733 A1 | 8/2008 | Al-Ali |
| 2008/0188760 A1 | 8/2008 | Al-Ali |
| 2008/0218153 A1 | 9/2008 | Patel et al. |
| 2008/0221418 A1 | 9/2008 | Al-Ali et al. |
| 2008/0221512 A1 | 9/2008 | Da Silva et al. |
| 2008/0275349 A1 | 11/2008 | Halperin et al. |
| 2008/0304580 A1 | 12/2008 | Ichiyama |
| 2009/0018409 A1 | 1/2009 | Banet et al. |
| 2009/0018429 A1 | 1/2009 | Saliga et al. |
| 2009/0018453 A1 | 1/2009 | Banet et al. |
| 2009/0036759 A1 | 2/2009 | Ault et al. |

(56) References Cited

U.S. PATENT DOCUMENTS

| | | |
|---|---|---|
| 2009/0043179 A1 | 2/2009 | Melker et al. |
| 2009/0093687 A1 | 4/2009 | Telfort et al. |
| 2009/0095926 A1 | 4/2009 | MacNeish, III |
| 2009/0112096 A1 | 4/2009 | Tamura |
| 2009/0160654 A1 | 6/2009 | Yang |
| 2009/0167332 A1 | 7/2009 | Forbes |
| 2009/0187065 A1 | 7/2009 | Basinger |
| 2009/0227882 A1 | 9/2009 | Foo |
| 2009/0240119 A1 | 9/2009 | Schwaibold et al. |
| 2009/0247848 A1 | 10/2009 | Baker |
| 2009/0247984 A1 | 10/2009 | Lamego et al. |
| 2009/0275844 A1 | 11/2009 | Al-Ali |
| 2009/0299157 A1 | 12/2009 | Telfort et al. |
| 2009/0312612 A1* | 12/2009 | Rantala ............... A61B 5/0205 600/301 |
| 2009/0326349 A1 | 12/2009 | McGonigle et al. |
| 2010/0004518 A1 | 1/2010 | Vo et al. |
| 2010/0004552 A1 | 1/2010 | Zhang et al. |
| 2010/0014761 A1* | 1/2010 | Addison ............ G06K 9/00516 382/207 |
| 2010/0016682 A1 | 1/2010 | Schluess et al. |
| 2010/0016693 A1 | 1/2010 | Addison |
| 2010/0030040 A1 | 2/2010 | Poeze et al. |
| 2010/0099964 A1 | 4/2010 | O'Reilly et al. |
| 2010/0130873 A1 | 5/2010 | Yuen |
| 2010/0204550 A1 | 8/2010 | Heneghan |
| 2010/0234718 A1 | 9/2010 | Sampath et al. |
| 2010/0261979 A1 | 10/2010 | Kiani |
| 2010/0270257 A1 | 10/2010 | Wachman et al. |
| 2010/0274099 A1 | 10/2010 | Telfort et al. |
| 2010/0295686 A1 | 11/2010 | Sloan |
| 2010/0298661 A1 | 11/2010 | McCombie et al. |
| 2010/0298730 A1 | 11/2010 | Taressenko et al. |
| 2010/0324377 A1 | 12/2010 | Woehrle |
| 2010/0331903 A1 | 12/2010 | Zhang |
| 2011/0001605 A1 | 1/2011 | Kiani |
| 2011/0009710 A1 | 1/2011 | Kroeger et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0040713 A1 | 2/2011 | Colman |
| 2011/0066062 A1 | 3/2011 | Banet et al. |
| 2011/0074409 A1 | 3/2011 | Stoughton |
| 2011/0082711 A1 | 4/2011 | Poeze et al. |
| 2011/0087081 A1 | 4/2011 | Kiani et al. |
| 2011/0105854 A1 | 5/2011 | Kiani et al. |
| 2011/0118561 A1 | 5/2011 | Tari et al. |
| 2011/0118573 A1 | 5/2011 | McKenna |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0172561 A1 | 7/2011 | Kiani et al. |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0222371 A1 | 9/2011 | Liu et al. |
| 2011/0230733 A1 | 9/2011 | Al-Ali et al. |
| 2011/0237911 A1 | 9/2011 | Lamego et al. |
| 2012/0016255 A1 | 1/2012 | Masuo |
| 2012/0059267 A1 | 3/2012 | Lamego et al. |
| 2012/0070013 A1 | 3/2012 | Vau |
| 2012/0101344 A1 | 4/2012 | Desjardins |
| 2012/0116175 A1 | 5/2012 | Al-Ali et al. |
| 2012/0123231 A1 | 5/2012 | O'Reilly |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0227739 A1 | 9/2012 | Kiani |
| 2012/0253140 A1 | 10/2012 | Addison et al. |
| 2012/0262298 A1 | 10/2012 | Bohm |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0045685 A1 | 2/2013 | Kiani |
| 2013/0046204 A1 | 2/2013 | Lamego |
| 2013/0041591 A1 | 3/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0116578 A1 | 5/2013 | An et al. |
| 2013/0128690 A1 | 5/2013 | Gopalan |
| 2013/0137936 A1 | 5/2013 | Baker, Jr. et al. |
| 2013/0162433 A1 | 6/2013 | Muhsin et al. |
| 2013/0190581 A1 | 7/2013 | Al-Ali et al. |
| 2013/0190595 A1 | 7/2013 | Oraevsky |
| 2013/0197328 A1 | 8/2013 | Diab et al. |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | Dalvi et al. |
| 2013/0296726 A1 | 11/2013 | Nievauer et al. |
| 2013/0317370 A1 | 11/2013 | Dalvi et al. |
| 2013/0324808 A1 | 12/2013 | Al-Ali et al. |
| 2013/0331670 A1 | 12/2013 | Kiani |
| 2013/0338461 A1 | 12/2013 | Lamego et al. |
| 2013/0345921 A1 | 12/2013 | Al-Ali et al. |
| 2014/0012100 A1 | 1/2014 | Lamego et al. |
| 2014/0025306 A1 | 1/2014 | Weber et al. |
| 2014/0034353 A1 | 2/2014 | Al-Ali et al. |
| 2014/0051953 A1 | 2/2014 | Lamego et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani et al. |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0206963 A1 | 7/2014 | Diab et al. |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |

(56) References Cited

U.S. PATENT DOCUMENTS

| | | |
|---|---|---|
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2015/0005600 A1 | 1/2015 | Blank et al. |
| 2015/0011907 A1 | 1/2015 | Purdon et al. |
| 2015/0018650 A1 | 1/2015 | Al-Ali et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2016/0196388 A1 | 7/2016 | Lamego |
| 2016/0283665 A1 | 9/2016 | Sampath et al. |
| 2016/0367173 A1 | 12/2016 | Dalvi et al. |
| 2017/0024748 A1 | 1/2017 | Haider |
| 2017/0042488 A1 | 2/2017 | Muhsin |
| 2017/0173632 A1 | 6/2017 | Al-Ali |
| 2017/0251974 A1 | 9/2017 | Shreim et al. |
| 2017/0311891 A1 | 11/2017 | Kiani et al. |
| 2018/0103874 A1 | 4/2018 | Lee et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |

FOREIGN PATENT DOCUMENTS

| | | |
|---|---|---|
| EP | 0659058 | 1/1999 |
| EP | 1207536 | 5/2002 |
| GB | 2358546 | 11/1999 |
| JP | 6214898 | 1/1987 |
| JP | 01-309872 | 6/1998 |
| JP | 10-155755 | 6/1998 |
| JP | 2001-50713 | 5/1999 |
| JP | 2001-321347 | 11/2001 |
| JP | 2002-028138 | 1/2002 |
| JP | 2003-329719 | 11/2003 |
| JP | 2006-516000 | 6/2006 |
| WO | WO 1994/005207 | 3/1994 |
| WO | WO 1994/013207 | 6/1994 |
| WO | WO 1995/029632 | 11/1995 |
| WO | WO 1999/053277 | 10/1999 |
| WO | WO 2000/010462 | 3/2000 |
| WO | WO 2001/034033 | 5/2001 |
| WO | WO 2001/078059 | 10/2001 |
| WO | WO 2001/097691 | 12/2001 |
| WO | WO 2002/003042 | 1/2002 |
| WO | WO 2003/058646 | 7/2003 |
| WO | WO 2003/087737 | 10/2003 |
| WO | WO 2004/000111 | 12/2003 |
| WO | WO 2004/004411 | 1/2004 |
| WO | WO 2004/034898 | 4/2004 |
| WO | WO 2005/096922 | 10/2005 |
| WO | WO 2005/096931 | 10/2005 |
| WO | WO 2005/099562 | 10/2005 |
| WO | WO 2006/097866 | 9/2006 |
| WO | WO 2008/017246 | 2/2008 |
| WO | WO 2008/080469 | 7/2008 |
| WO | WO 2008/148172 | 12/2008 |
| WO | WO 2009/093159 | 7/2009 |
| WO | WO 2009/137524 | 11/2009 |

OTHER PUBLICATIONS

US 9,579,050 B2, 02/2017, Al-Ali (withdrawn)

Cannesson et al., "Relation Between Respiratory Variations in Pulse Oximetry Plethysmographic Waveform Amplitude and Arterial Pulse Pressure in Ventilated Patients", Critical Care 2005, Aug. 23, 2005, pp. R562-R568.

GE Healthcare, "Transport Pro™ Patient Monitor Operator's Manual" Apr. 9, 2007, in 286 pages.

Hsu, "Signals and Systems", Schaum's Theory and Problems, 1995, Ch. 3, p. 121.

Szecsei, "Homework Helpers Basic Math and Pre-Algebra", 2006, The Career Press, p. 133.

Analog Devices, 12-Bit Serial Input Multiplying D/A Converter, Product Data Sheet, 2000.

Chambrin, M-C.; "Alarms in the intensive care unit: how can the number of false alarms be reduced?"; Critical Care Aug. 2001, vol. 5 No. 4; p. 1 -5.

Eldor et al., "A device for monitoring ventilation during anaesthesia; the paratracheal audible respiratory monitor", Canadian Journal of Anaesthesia, 1990, vol. 9, No. 1, p. 95-98.

Gorges, M. et al.; "Improving Alarm Performance in the Medical Intensive Care Unit Using Delays and Clinical Context"; Technology, Computing, and Simulation; vol. 108, No. 5, May 2009; p. 1546-1552.

Imhoff, M et al.; "Alarm Algorithms in Critical Care Monitoring"; Anesth Analg 2006;102:1525-37.

International Search Report & Written Opinion, PCT Application PCT/US2010/052758, dated Feb. 10, 2011; 12 pages.

International Search Report & Written Opinion, PCT Application PCT/US2010/058981, dated Feb. 17, 2011; 11 pages.

International Search Report and Written Opinion issued in application No. PCT/US2010/052756 dated Feb. 6, 2012.

(56) References Cited

OTHER PUBLICATIONS

International Search Report, PCT Application PCT/CA2003/000536, dated Dec. 11, 2003; 2 pages.
International Search Report, PCT Application PCT/US2009/069287, dated Mar. 30, 2010; 7 pages.
Japanese Office Action for JP Application No. 2007-506626 dated Mar. 1, 2011.
Sierra et al., Monitoring Respiratory Rate Based on Tracheal Sounds. First Experieances, Proceedings of the 26th Annual Int'l Conf. of the IEEE EMBS (Sep. 2004), 317-320.
Watt, R. C.; "Alarms and Anesthesia. Challenges in the design of Intelligent systems for Patient Monitoring"; IEEE Engineering in Medicine and biology; Dec. 1993, p. 34-41.
Welch Allyn, ECG ASIC, Product Data Sheete, 2001.
Supplementary Partial European Search Report for International Application No. 05732095.4, dated Jun. 26, 2009 in 4 pages.
Theimer et al., "Definitions of audio features for music content description", Algorithm Engineering Report TR08-2-001, Feb. 2008.
Stewart, C., Larson, V., "Detection and classification of acoustic signals from fixed-wing aircraft," Systems Engineering, CH3051-0/91/0000-0025, IEEE, 1991.
Johnston, Development of a Signal Processing Library for Extraction of Sp02, HR, HRV, and RR from Photoplethysmographic Waveforms, Thesis: Degree of Master of Science, Worcester Polytechnic Institute, date of presentation/defense Jul. 17, 2006, date listed Jul. 27, 2006.

* cited by examiner

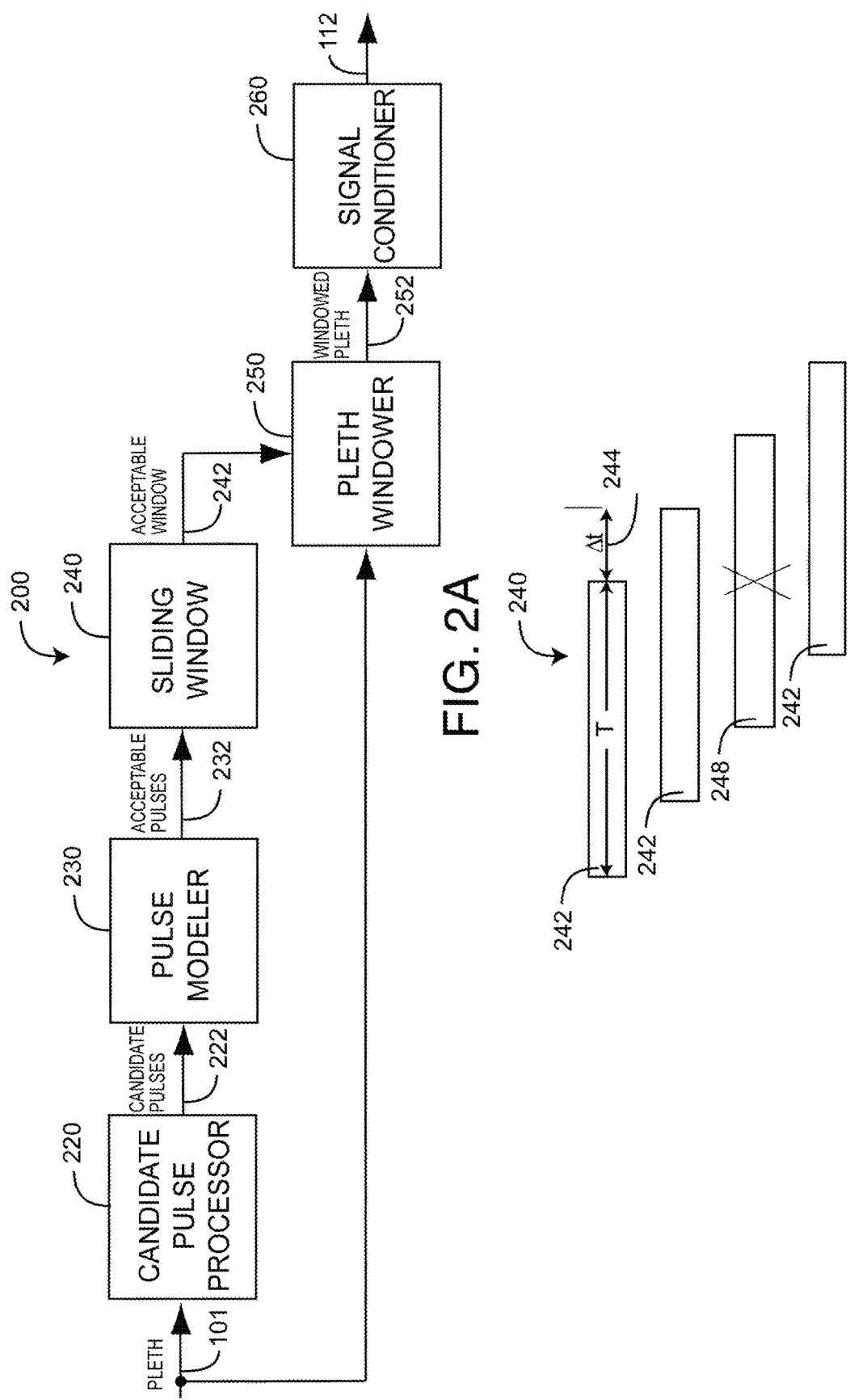

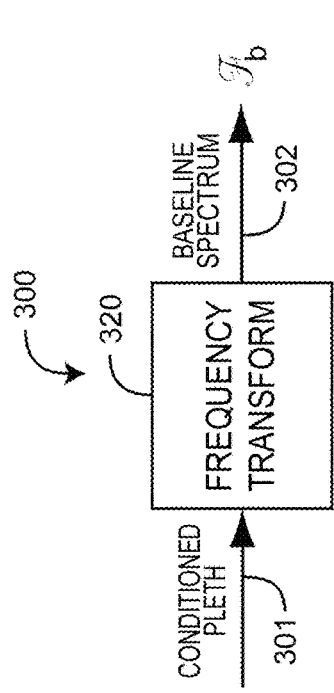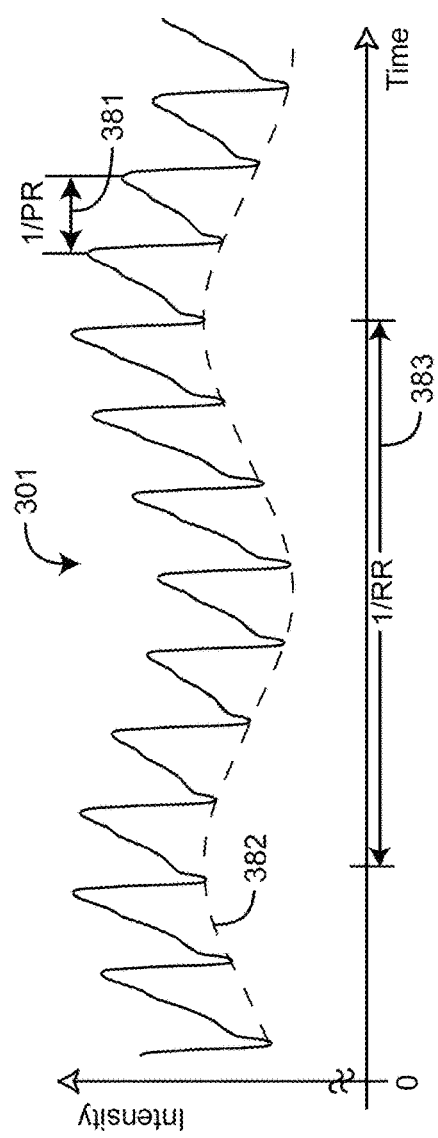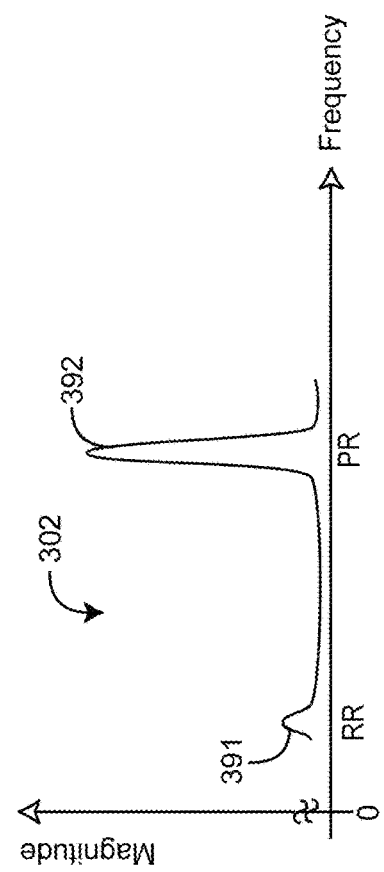
FIG. 3A
FIG. 3B
FIG. 3C

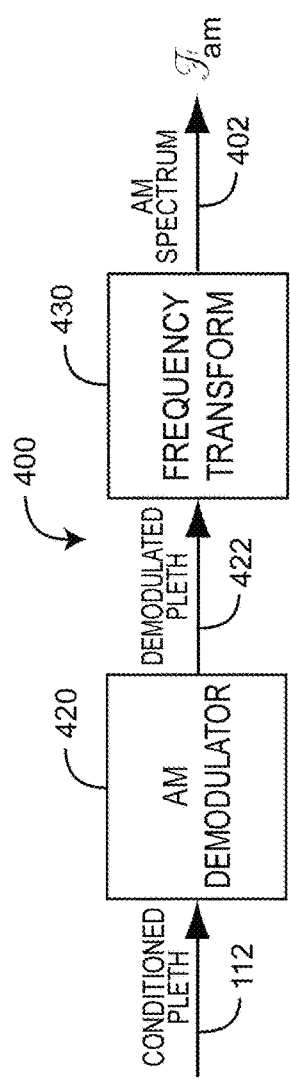
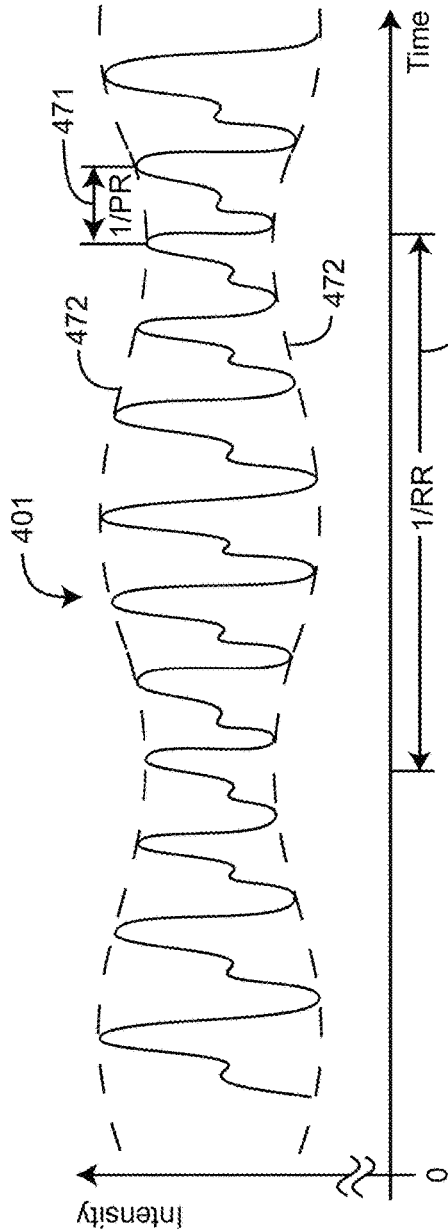
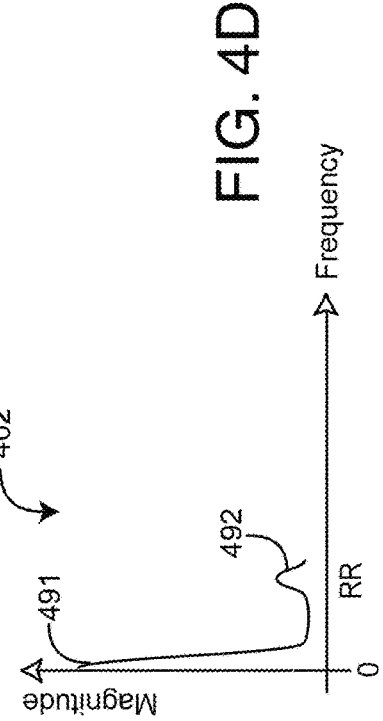
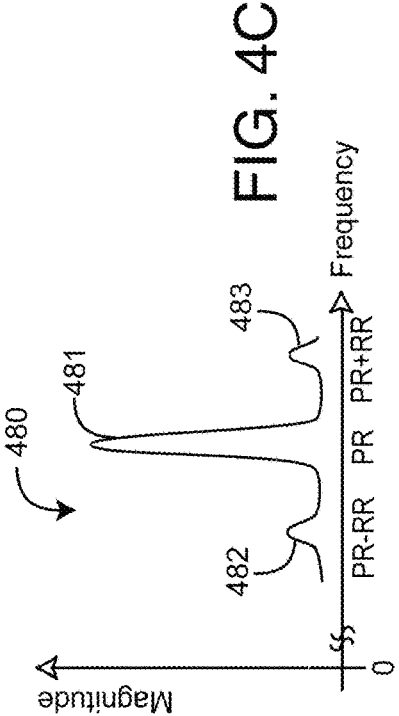
FIG. 4A
FIG. 4B
FIG. 4C
FIG. 4D

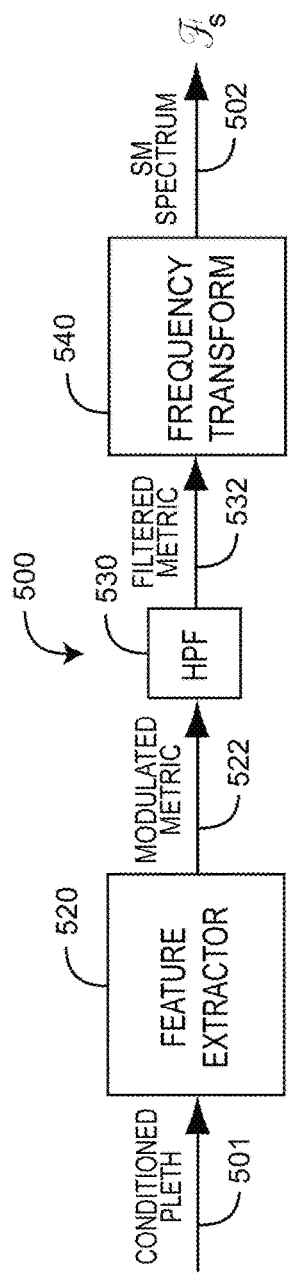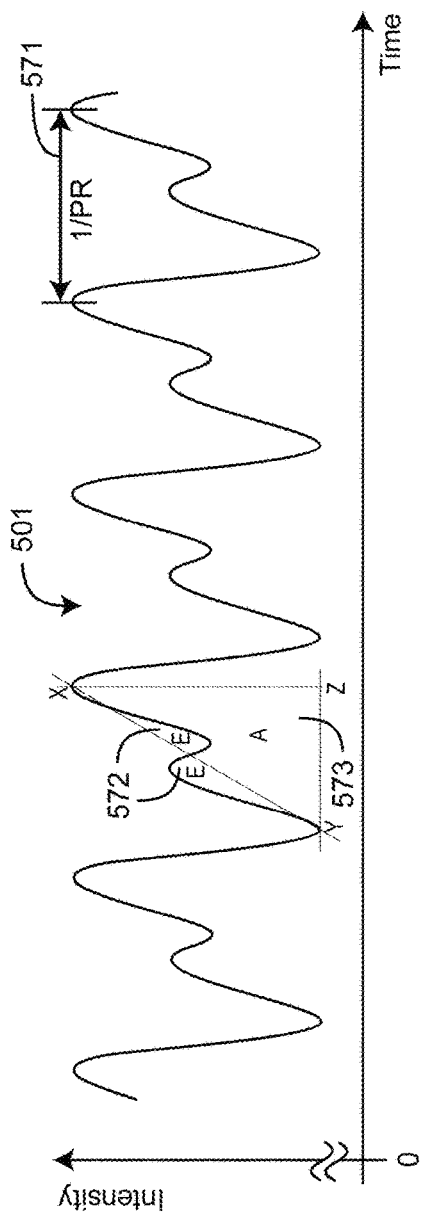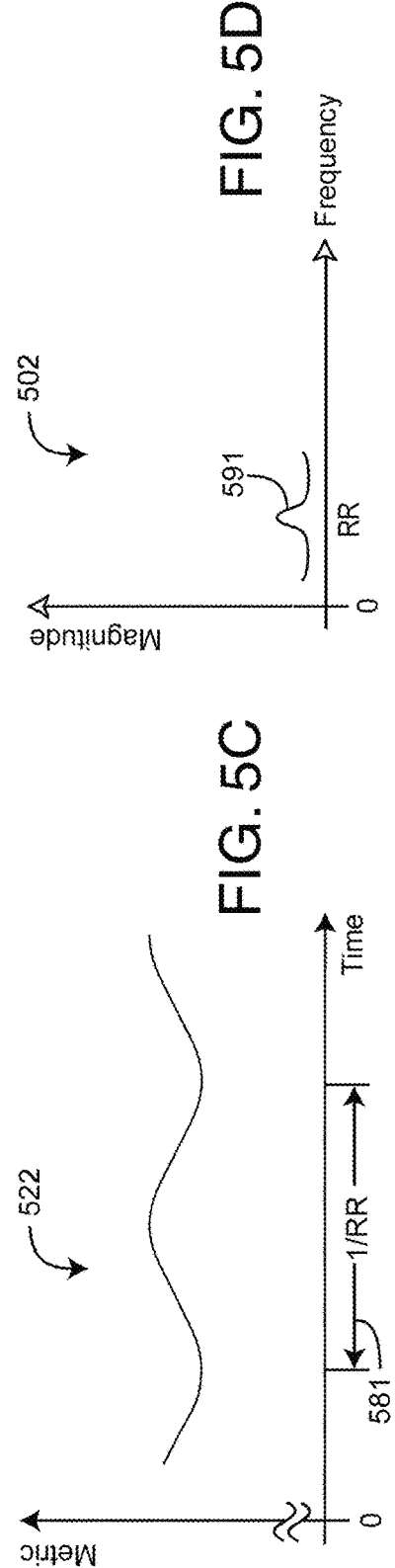

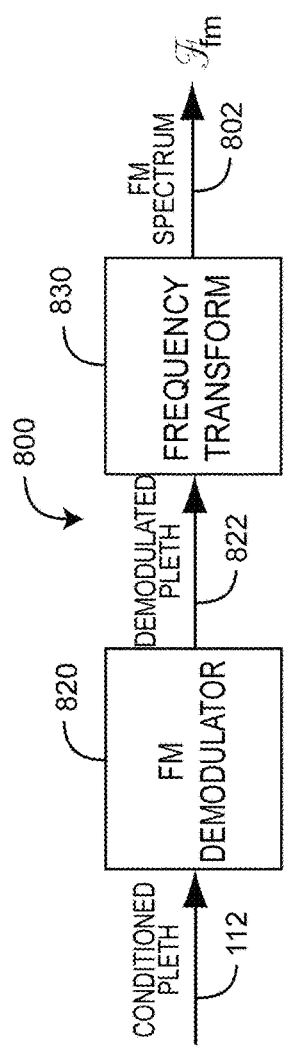
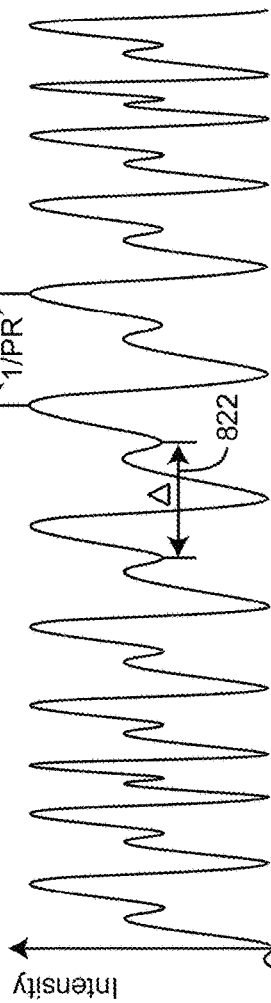
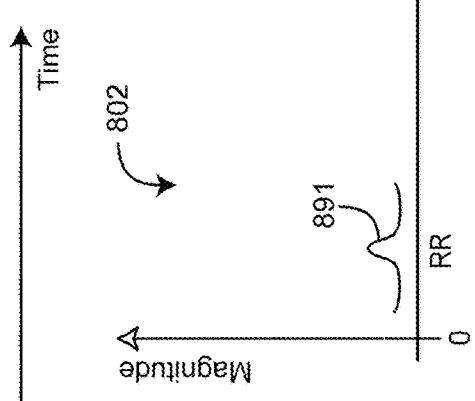
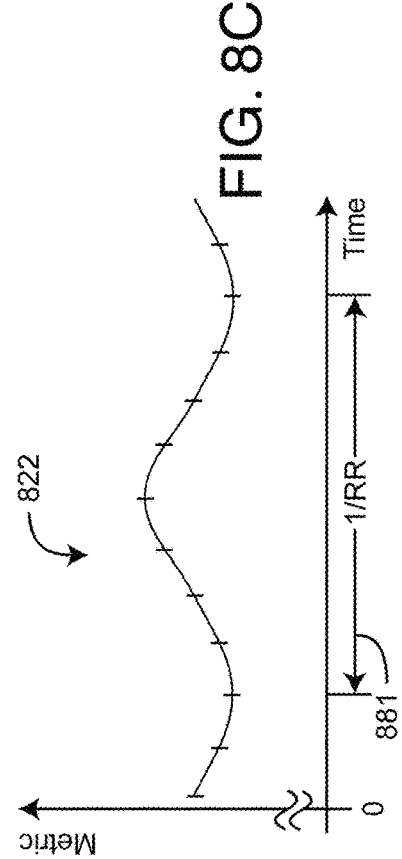
FIG. 8A
FIG. 8B
FIG. 8C
FIG. 8D

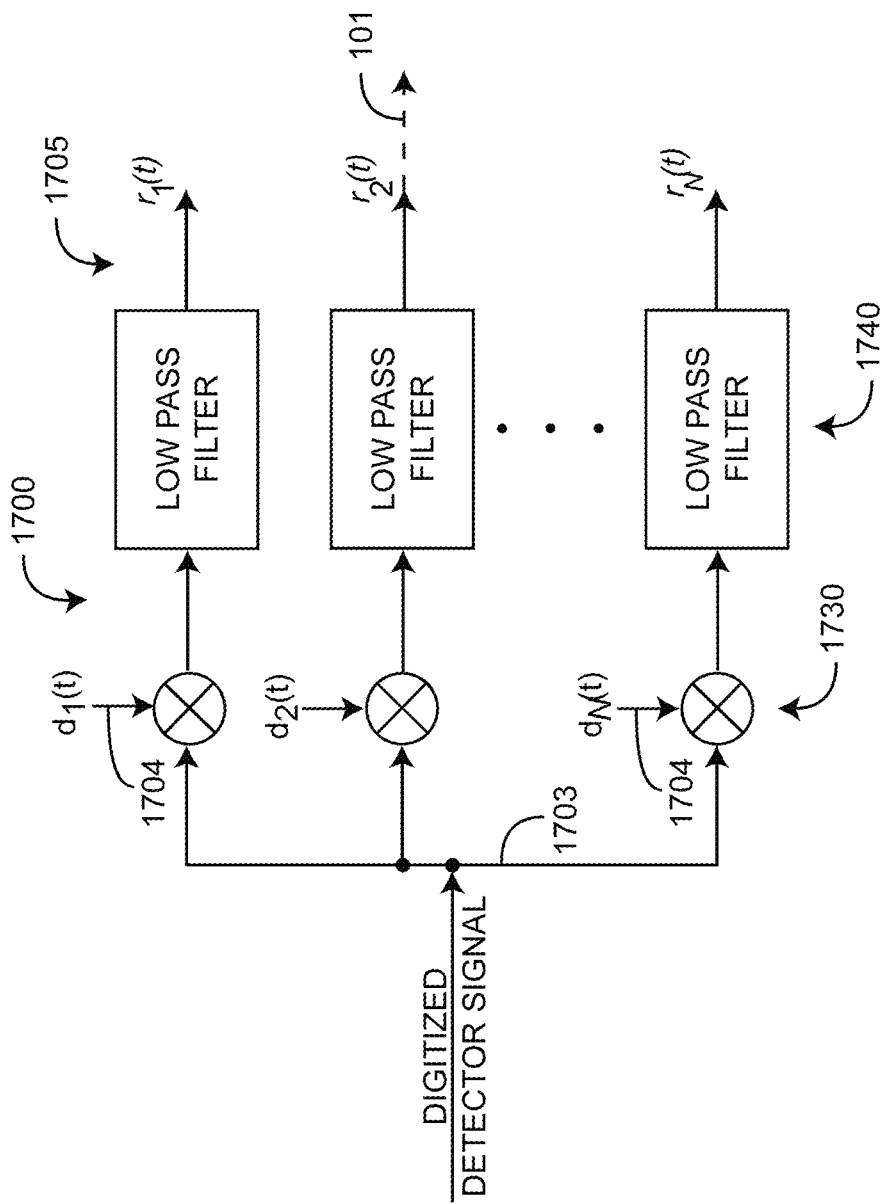

PLETHYSMOGRAPHIC RESPIRATION RATE DETECTION

PRIORITY CLAIM TO RELATED PROVISIONAL APPLICATIONS

The present application is a continuation of U.S. patent application Ser. No. 15/095,912, filed Apr. 11, 2016, titled Plethysmographic Respiration Rate Detection, which is a divisional of U.S. patent application Ser. No. 13/076,423, filed Mar. 30, 2011, titled Plethysmographic Respiration Processor, which claims priority benefit under 35 U.S.C. § 119(e) to U.S. Provisional Patent Application No. 61/319,256, filed Mar. 30, 2010, titled Plethysmographic Respiration Processor and U.S. Provisional Patent Application No. 61/364,141, filed Jul. 14, 2010, titled Plethysmographic Respiration Detector; all of the above-cited patent applications are hereby incorporated by reference herein.

BACKGROUND OF THE INVENTION

Pulse oximetry is a widely accepted noninvasive procedure for measuring the oxygen saturation level of arterial blood, an indicator of a person's oxygen supply. A typical pulse oximetry system utilizes an optical sensor clipped onto a fingertip to measure the relative volume of oxygenated hemoglobin in pulsatile arterial blood flowing within the fingertip. Oxygen saturation ($SpO_2$), pulse rate and a plethysmograph waveform, which is a visualization of pulsatile blood flow over time, are displayed on a monitor accordingly.

Conventional pulse oximetry assumes that arterial blood is the only pulsatile blood flow in the measurement site. During patient motion, venous blood also moves, which causes errors in conventional pulse oximetry. Advanced pulse oximetry processes the venous blood signal so as to report true arterial oxygen saturation and pulse rate under conditions of patient movement. Advanced pulse oximetry also functions under conditions of low perfusion (small signal amplitude), intense ambient light (artificial or sunlight) and electrosurgical instrument interference, which are scenarios where conventional pulse oximetry tends to fail.

Advanced pulse oximetry is described in at least U.S. Pat. Nos. 6,770,028; 6,658,276; 6,157,850; 6,002,952; 5,769,785 and 5,758,644, which are assigned to Masimo Corporation ("Masimo") of Irvine, Calif. and are incorporated by reference herein. Corresponding low noise optical sensors are disclosed in at least U.S. Pat. Nos. 6,985,764; 6,813,511; 6,792,300; 6,256,523; 6,088,607; 5,782,757 and 5,638,818, which are also assigned to Masimo and are also incorporated by reference herein. Advanced pulse oximetry systems including Masimo SET® low noise optical sensors and read through motion pulse oximetry monitors for measuring $SO_2$, pulse rate (PR) and perfusion index (PI) are available from Masimo. Optical sensors include any of Masimo LNOP®, LNCS®, SofTouch™ and Blue™ adhesive or reusable sensors. Pulse oximetry monitors include any of Masimo Rad-8®, Rad-5®, Rad®-5v or SatShare® monitors.

Advanced blood parameter measurement systems are described in at least U.S. Pat. No. 7,647,083, filed Mar. 1, 2006, titled Multiple Wavelength Sensor Equalization; U.S. patent application Ser. No. 11/367,036, filed Mar. 1, 2006, titled Configurable Physiological Measurement System; U.S. patent application Ser. No. 11/367,034, filed Mar. 1, 2006, titled Physiological Parameter Confidence Measure and U.S. patent application Ser. No. 11/366,208, filed Mar. 1, 2006, titled Noninvasive Multi-Parameter Patient Monitor, all assigned to Masimo Laboratories, Irvine, Calif. (Masimo Labs) and all incorporated by reference herein. Advanced blood parameter measurement systems include Masimo Rainbow® SET, which provides measurements in addition to $SO_2$, such as total hemoglobin (SpHb™), oxygen content (SpOC™), methemoglobin (SpMet®), carboxyhemoglobin (SpCO®) and PVI®. Advanced blood parameter sensors include Masimo Rainbow® adhesive, ReSposable™ and reusable sensors. Advanced blood parameter monitors include Masimo Radical-7™, Rad-87™ and Rad-57™ monitors, all available from Masimo. Such advanced pulse oximeters, low noise sensors and advanced blood parameter systems have gained rapid acceptance in a wide variety of medical applications, including surgical wards, intensive care and neonatal units, general wards, home care, physical training, and virtually all types of monitoring scenarios.

SUMMARY OF THE INVENTION

Advantageously, a plethysmographic respiration processor provides respiration rate readings based upon optical properties of pulsatile blood flow. The respiration rate so derived may be used alone or combined with respiration rate derived by various other means including, but not limited to, microphones or other acoustic sensors located to respond to various body sounds; humidity sensors located to respond to inhalation/exhalation moisture; thermistors and photodiodes located to respond to inhalation/exhalation air temperature; capacitance sensors located to respond to inhalation/exhalation air pressure; and venturi effect sensors located to respond to inhalation/exhalation air flow. In a particularly advantageous embodiment, a plethysmographic respiration detector is used in conjunction with an acoustic monitor or combined blood parameter and acoustic monitor, such as a Masimo Rainbow® SET platform and an acoustic respiration rate (RRa™) sensor available from Masimo, so as to improve the accuracy of, robustness of, or otherwise supplement acoustic-derived respiration rate measurements or other acoustic-derived respiration parameters.

One aspect of a plethysmographic respiration processor is responsive to respiration affecting blood volume and a corresponding detected intensity waveform measured with an optical sensor at a blood perfused peripheral tissue site so as to provide a measurement of respiration rate. The plethysmographic respiration detector comprises a preprocessor, processors and decision logic. The preprocessor identifies a windowed pleth corresponding to a physiologically acceptable series of plethysmograph waveform pulses. The processors derive various spectrums of the windowed pleth. Each of the processors is configured so that its corresponding spectrum is particularly responsive to a specific respiratory effect on the windowed pleth. The decision logic determines a respiration rate based upon matching features of at least two of the spectrums.

In various embodiments, the processors comprise a baseline processor that inputs the windowed pleth and outputs a "baseline" spectrum. The baseline processor has a first signal conditioner and a first frequency transform. The first signal conditioner generates a first conditioned pleth from the windowed pleth. The first frequency transform inputs the first conditioned pleth and generates the baseline spectrum.

The processors further comprise an amplitude modulation (AM) processor that inputs the windowed pleth and outputs an "AM" spectrum. The AM processor has a second signal conditioner that generates a second conditioned pleth from the windowed pleth. A demodulator AM demodulates the second conditioned pleth to generate a demodulated pleth. A second frequency transform inputs the demodulated pleth and generates the AM spectrum.

The processors further comprise a shape modulation (SM) processor that inputs the windowed pleth and outputs a "SM" spectrum. The SM processor has a third signal conditioner that generates a third conditioned pleth from the windowed pleth. A feature extractor generates a modulated metric from the third conditioned pleth. A third frequency transform generates the SM spectrum from the modulated metric.

The decision logic has a peak detector, a comparator and a respiration rate output. The peak detector operates on at least two of the baseline spectrum, the AM spectrum and the SM spectrum so as to determine local maximums. The comparator determines if there are any local maximums from the at least two of the spectrums that occur at matching frequencies within a predetermined tolerance. A respiration rate output is generated if the comparator finds at least a two-way match. A smoother operates on multiple respiration rate outputs derived over a sliding series of the windowed pleths so as to derive a smoothed respiration rate output. A tested condition rejects the respiration rate output if it differs from the smoothed respiration rate output by more than a predetermined amount.

Another aspect of a respiration rate processor is inputting a plethysmograph waveform, determining a baseline spectrum responsive to a respiratory-induced baseline shift of the plethysmograph waveform, determining an amplitude modulation (AM) spectrum responsive to a respiratory-induced amplitude modulation of the plethysmograph waveform, determining a shape modulation (SM) spectrum responsive to a respiratory-induced shape modulation of the plethysmograph waveform, and matching at least two of the baseline, AM and SM spectrums so as to derive a respiration rate. In an embodiment, determining a baseline spectrum comprises frequency transforming the plethysmograph waveform. In an embodiment, determining an AM spectrum comprises demodulating the plethysmograph waveform so as to generate a demodulated pleth; and frequency transforming the demodulated pleth. In an embodiment, determining a SM spectrum comprises feature extracting the plethysmograph waveform so as to generate a modulated metric and frequency transforming the modulated metric.

In various other embodiments, matching comprises detecting peaks in at least two of the spectrums, comparing the detected peaks so as to find one peak from each of the at least two spectrums occurring at a particular frequency and outputting the particular frequency as the respiration rate. Windowed pleths are defined by a sliding window of acceptable portions of the plethysmograph waveform. The respiration rate output is smoothed based upon a median respiration rate calculated over multiple ones of the windowed pleths. The particular frequency is rejected if it is not within a predetermined difference of the smoothed respiration rate.

A further aspect of a respiration rate processor is a baseline processor, an AM processor, a SM processor and decision logic. The baseline processor identifies a respiration-induced baseline shift in a plethysmograph waveform. The AM processor identifies a respiration-induced amplitude modulation of the plethysmograph waveform. The SM processor identifies a respiration-induced shape modulation of the plethysmograph waveform. The decision logic compares the respiration-induced baseline shift, amplitude modulation and shape modulation so as to derive a respiration rate.

In various embodiments, the baseline processor generates a baseline spectrum from a first frequency transform of the plethysmograph waveform. The AM processor generates an AM spectrum from a second frequency transform of demodulated plethysmograph waveform. The SM processor generates an SM spectrum from a third frequency transform of a modulated metric extracted from the plethysmograph waveform. Decision logic has a peak detector and a comparator. The peak detector determines local maximums in each of the baseline spectrum, AM spectrum and SM spectrum. In an embodiment, the comparator determines a three-way match in the frequency of the local maximums in the spectrums. In an embodiment, the comparator determines a two-way match in the frequency of the local maximums in the spectrums, and a condition for accepting the two-way match compares a respiration rate determined by the two-way match to a smoothed respiration rate.

A further aspect of a plethysmographic respiration processor is responsive to respiratory modulation of a blood volume waveform or corresponding detected intensity waveform measured with an optical sensor at a blood perfused peripheral tissue site so as to provide a measurement of a respiration parameter. A demodulator processes a sensor signal so as to generate a plethysmograph waveform. A pulse processor identifies candidate pulses from the plethysmograph waveform. A pulse modeler identifies physiologically acceptable ones of the candidate pulses. The plethysmographic respiration processor has a feature extractor, a normalizer and a feature analyzer. The feature extractor processes the acceptable pulses so as to calculate pulse features. The normalizer compares the pulse features so as to calculate a pulse parameter. The feature analyzer calculates a respiration parameter from the pulse parameter.

In various embodiments, the pulse features comprise a difference (E) between an acceptable pulse and a triangular pulse estimate; the pulse features comprise an area (A) under a triangular pulse; or the pulse features are calculated with respect to a diastolic (d) portion of an acceptable pulse and a corresponding diastolic portion of a triangular pulse. In various embodiments, the normalizer compares a diastolic difference (Ed) with a diastolic area (Ad) or the normalizer calculates Ed/Ad. In an embodiment, the feature analyzer determines the frequency spectrum of Ed/Ad so as to determine a respiration rate.

Yet another aspect of a plethysmographic respiration processor detects a tissue site response to optical radiation having a plurality of wavelengths, demodulates the response according to wavelength so as to generate a corresponding plurality of plethysmograph waveforms, identifies acceptable pulses from at least one of the waveforms and calculates a respiration parameter from the acceptable pulses. To calculate a respiration parameter, in various embodiments the processor estimates an acceptable pulse with a triangular pulse and determines a systolic portion and a diastolic portion of the acceptable pulse and the triangular pulse; compares the triangular to the acceptable pulse so as to define pulse features; normalizes the pulse features according to the systolic and diastolic portions so as to generate a pulse parameter; or analyzes the pulse parameter to derive a respiration parameter. The comparing may comprise differencing the acceptable pulse and the triangular pulse over the diastolic portion. The analyzing may comprise transforming the pulse parameter to a frequency parameter and outputting a respiration rate according to a maximum of the frequency parameter.

Additional aspects of plethysmographic respiration processor has a pulse input having physiologically acceptable pleth pulses derived from a plethysmograph waveform. A feature extractor extracts pulse features from the pulse input. The pulse features are modulated by respiration. A normalizer calculates a pulse parameter from the relative magnitude of a first one of the pulse features compared with a second one of the pulse features. A feature analyzer calculates a respiration parameter from the pulse parameter.

In various embodiments, the feature extractor may calculate a difference between a triangular pulse estimate and a corresponding pleth pulse. The feature may also calculate an area under a portion of the triangular pulses. The processor may differentiate between a systolic pulse feature and a diastolic pulse feature. The feature extractor may calculate an apex angle of the slope portion of a triangular pulse estimate. The feature analyzer may perform a frequency transform to extract a respiration rate from the pulse parameter.

BRIEF DESCRIPTION OF THE DRAWINGS

FIGS. 2A-B are a block diagram of a pre-processor embodiment and a time illustration of a sliding window, respectively;

FIGS. 3A-C are a block diagram of a baseline processor, an intensity versus time graph of a baseline modulated pleth, and a baseline frequency spectrum, respectively;

FIGS. 4A-D are a block diagram of an AM processor, an intensity versus time graph of an AM pleth, and AM pleth frequency spectrum and a demodulated pleth frequency spectrum, respectively;

FIGS. 5A-D are a block diagram of an SM processor, an intensity versus time graph of an SM pleth, and graph of a shape metric versus time; and a shape metric frequency spectrum, respectively;

FIG. 8A-D are a block diagram of an FM processor, an intensity versus time graph of an FM pleth, and graph of a dicrotic-notch based FM metric versus time; and a FM metric frequency spectrum, respectively;

FIG. 17 is a block diagram of a modulated plethysmograph demodulator.

DETAILED DESCRIPTION OF THE PREFERRED EMBODIMENTS

Figure 1:
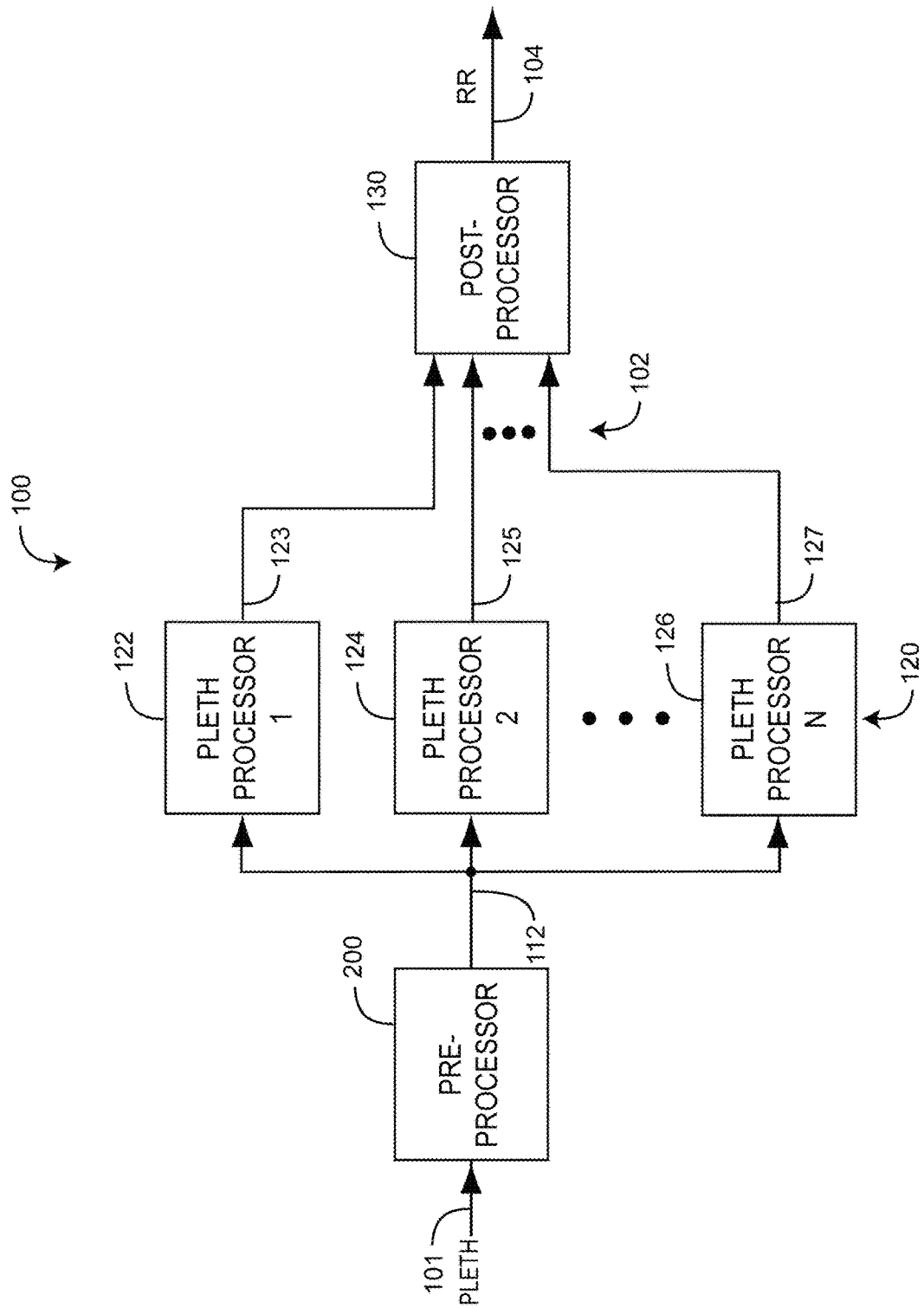
FIG. 1 is a block diagram of a plethysmographic respiration processor embodiment.

FIG. 1 illustrates a plethysmographic respiration processor 100 embodiment having a plethysmograph waveform (pleth) input 101 and a respiration rate (RR) output 104. The pleth respiration processor 100 includes a preprocessor 200, one or more pleth processors 120 and a post processor 130. The pleth 101 is derived from an optical sensor attached to a tissue site, which is in communications with a pulse oximeter or blood parameter monitor, as described with respect to FIGS. 14-17, below. The pre-processor 200 derives acceptable pleths 112, as described in detail with respect to FIGS. 2A-B, below. The pleth processor(s) 120 each operate on acceptable pleths 112 so as to generate respiration-rated parameters 102 responsive to a person's respiration. The pleth processors 120 may operate in the time domain, the frequency domain or a mix of time or frequency domains. Pleth processors 120 are described in detail with respect to FIGS. 3-8, below. The post-processor 130 resolves or otherwise verifies the respiration-related parameters 102 so as to derive a respiration rate and, perhaps, averages, smoothes or otherwise filters that respiration rate so as to generate the respiration rate (RR) 104 output. Advantageously, this optical sensor derived RR may be used to derive a less intrusive measure of respiration rate or used in combination with acoustic, mechanical, electrical, temperature or other sensors and monitors so as to determine a more accurate or robust measure of respiration rate. Although described herein as deriving a respiration rate, a plethysmographic respiration processor 100 output may be similarly expressed as a respiration or a breathing frequency or interval, among others.

FIGS. 2A-B illustrate a pre-processor 200 having a pleth 101 input and generating a conditioned pleth 112, as described below. The pre-processor 200 has a candidate pulse processor 220, a pulse modeler 230, a sliding window 240, a pleth windower 250 and a signal conditioner 260. A single pleth channel is selected from a multiple demodulated pleths 1705 (FIG. 17) as a representative pleth 101 input. In an embodiment, the representative pleth channel corresponds to the IR wavelength channel of a (two wavelength) pulse oximeter.

As shown in FIG. 2A, the pleth 101 is fed into a candidate pulse processor 220 that removes noise and artifacts and identifies the start and end of pulses that conform to various tests of physiological acceptability. In an embodiment, the candidate pulse processor 220 has curvature, low-pass filter and edge finder components that remove waveform features that do not correspond to the steep inflow phase during ventricular systole or the longer outflow phase during diastole, including the characteristic dicrotic notch and miscellaneous waveform curvature changes. Accordingly, the candidate pulse processor 220 identifies "edges" within an input waveform segment that connect a peak and subsequent valley of a pleth pulse. The candidate pulse processor 220 also has delta T, zero crossing, amplitude threshold and slope checks so as to eliminate certain of the edges that were identified by the curvature, filter and edge finder components that do not meet certain conditions. The delta T discards all the edges that are either too slow or too quick to be physiological. The zero crossing check eliminates all edges that do not cross the zero line, such as small bumps that are not peaks or valleys. The amplitude threshold check removes larger "bumps" than the zero crossing check, such as dicrotic notches. The slope check is based on the observation that in a physiological pulse, the ventricular contraction, i.e. descending pulse portion, is steeper than any subsequent trend in the ascending pulse portion. The pulse finder transforms the edges remaining after the various edge checks into candidate pulses 222, which are fed into the pulse modeler 230.

Also shown in FIG. 2A, the pulse modeler 230 takes the candidate pulses 222 and identifies which of these are acceptable pulses 232, which satisfy an internal model for a physiological plethysmographic waveform. Although the candidate pulse processor 220 performs a series of checks on edges, the pulse modeler 230 performs a series of checks on pulse features. The first component of the pulse modeler calculates relevant pulse features. The remainder of the pulse modeler checks these pulse features to identify physiologically acceptable features. The pulse features component extracts three items of information about the input candidate pulses that are needed for downstream processing by the other components of the pulse modeler including pulse starting point, period and signal strength. The downstream components include a max BPM check, a stick model check, an angle check, a ratio check and a signal strength check. The maximum beats-per-minute (max BPM) check discards pulses having a period that is below a minimum number of samples. The stick model check discards pulses where the corresponding waveform does not fit a stick model. The angle check is based on computing the angle of a normalized slope for the ascending portion of a pulse so as to discard pulses that are extremely asymmetric. The ratio check removes pulses in which the ratio between the duration of the ascending pulse portion and the duration of the descending pulse portion is less than a certain threshold. The signal strength check assigns a confidence value to each pulse, based on its signal strength, and low confidence pulses are discarded. A pulse processor 220 and a pulse modeler 230 are described in U.S. Pat. No. 6,463,311 titled Plethysmograph Pulse Recognition Processor, issued Oct. 8, 2002, assigned to Masimo Corporation and incorporated by reference herein.

Further shown in FIGS. 2A-B, the sliding window 240 defines a series of fixed-time-length (T) samples ("windows") of pleth, where each window 242 is shifted from the previous window by a fixed time interval (Δt) 244. In an embodiment, each window is T=2125 samples (34 sec) in length at 16 msec per sample (62.5 Hz sample rate), where successive windows are shifted by Δt=2 sec. Each window is either accepted 242 or rejected 248 as designated by an acceptable window 242 output. The pleth windower 250 utilizes the acceptable windows 242 designation to accept a corresponding section of the "raw" pleth 101 input and generate a windowed (raw) pleth 252 output. That is, the pre-processor 200 advantageously allows downstream processing to operate directly on the demodulated pleth while discarding those raw pleth sections that are deemed unacceptable, based upon various pleth models and checks as described above. In an embodiment, the signal conditioner 260 demeans/detrends and bandpass filters the windowed pleth 252 to generate a conditioned pleth 112 output. In an embodiment, the bandpass filter is an IIR filter having a 12-240 bpm (beats per minute) passband. In another embodiment described below with respect to FIG. 9, below, a pre-processor 200 generates windowed features from acceptable pulses derived from the pleth 101 input.

FIGS. 3A-B illustrate a baseline processor 300 that derives a "baseline" spectrum $F_b$ 302 responsive to a respiration-induced baseline shift in a pleth. As shown in FIG. 3A, the baseline processor 300 has a conditioned pleth 301 input and generates a corresponding baseline spectrum $F_b$ 302. As shown in FIG. 3B, the conditioned pleth 301 has a pleth period 381 inversely related to pulse rate (PR). Under certain conditions, an individual's respiration induces a cyclical shift in the pleth baseline 382. The cyclical shift period 383 is inversely related to respiration rate (RR). As shown in FIG. 3C, a frequency spectrum 302 of the baseline-shifted pleth 301 includes a relatively large pulse rate (PR) peak 392 and a relatively small respiration rate (RR) peak 391.

In other embodiments, a baseline processor 300 employs a time domain calculation of the conditioned pleth 301 that determines the period 383 of a cyclical baseline shift and hence respiration rate. Such a time domain calculation may be based upon envelope detection of the conditioned pleths 301, such as a curve-fit to the peaks (or valleys) of the pleth pulses. Measurements of a cyclical variation in a plethysmograph baseline are described in U.S. patent application Ser. No. 11/221,411 titled Noninvasive Hypovolemia Monitor, filed Sep. 6, 2005 and published as US 2006/0058691 A1, assigned to Masimo and incorporated by reference herein.

FIGS. 4A-B illustrate an AM processor 400 that derives an "AM" spectrum $F_{am}$ 402 responsive to a respiration-induced amplitude modulation of the pleth. As shown in FIG. 4A, the AM processor 400 has a conditioned pleth 401 input and generates a corresponding AM spectrum $F_{am}$ 402 that is responsive to a demodulated pleth 422. In an embodiment, the demodulator 420 squares, low pass filters (LPF) and square-roots the conditioned pleth 401 to generate a demodulated pleth 422. In an embodiment, the frequency transformation 430 utilizes a Hamming window, a chirp-Z FFT algorithm and a magnitude calculation so as to generate an AM spectrum 402 for the demodulated pleth 422.

As shown in FIG. 4B, a pleth 401 has a pleth period 471 inversely related to pulse rate (PR). Under certain conditions, an individual's respiration amplitude modulates (AM) 472 the plethysmograph 401. In particular, the modulation period 473 is inversely related to respiration rate (RR). As shown in FIG. 4C, a spectrum 480 of the pleth 401 includes a pulse rate (PR) peak 481 and respiration sidebands 482, 483 displaced by RR on either side of the PR peak 481. As shown in FIG. 4D a spectrum 402 of the demodulated pleth 422 includes a DC peak 491 resulting from the demodulated pulse rate "carrier" translated to DC and a respiration rate (RR) peak 492 resulting from the demodulated sidebands 482, 483.

An AM processor 400 is described above as demodulating 420 a conditioned pleth 401. In other embodiments, a time domain calculation of the conditioned pleth 401 determines the respiration modulation period 473 and hence the respiration rate. That time domain calculation may be based upon envelope detection of the conditioned pleth 401, such as a curve-fit to the peaks (or valleys) of the plethysmograph or, alternatively, the peak-to-peak variation. Measurements of variation in a plethysmograph envelope are described in U.S. patent application Ser. No. 11/952,940 titled Plethysmograph Variability Processor, filed Dec. 7, 2007 and published as US 2008/0188760 A1, assigned to Masimo and incorporated by reference herein.

FIGS. 5A-D illustrate a shape modulation (SM) processor 500 that derives an "SM" spectrum $F_s$ 502 responsive to a respiration-induced shape modulation of the pleth. As shown in FIG. 5A, the SM processor 500 has a conditioned pleth 501 input and generates a corresponding SM spectrum $F_s$ 502. In an embodiment, the SM processor 500 includes a feature extractor 520, a high pass filter (HPF) 530 and a frequency transform 540. In another embodiment, the SM processor includes the feature extractor 520 and a frequency transform 540, but excludes the high pass filter 530. The feature extractor 520 generates a shape-based modulated metric 522, such as E/A described below. In an embodiment, the HPF 530 is a time domain difference filter that calculates $Y_{n+1} - Y_n$ so as to remove an erroneous first (low frequency) peak in the SM spectrum $F_s$ 502. In an embodiment, the frequency transformation 540 utilizes a Hamming window, a chirp-Z FFT algorithm and a magnitude calculation so as to generate the SM spectrum 502 for each windowed conditioned pleth 501.

As shown in FIG. 5B, a pleth 501 has a pleth period 571 inversely related to pulse rate (PR). Under some circumstances, an individual's respiration modulates the shape of each pleth pulse. This modulation may be described in terms of a predefined pleth feature or "shape metric." In an advantageous embodiment, a shape metric is defined by a difference or "error" E 572 between the diastolic portion of a pleth pulse and its corresponding triangular pulse approximation, normalized by the area A 573 under the triangular pulse approximation.

As shown in FIG. 5C, a respiration-modulated shape metric 522 has a cyclical period 581 inversely related to respiration rate (RR). As shown in FIG. 5D, a spectrum 502 of the modulated shape metric 522 includes a respiration rate (RR) peak 591.

A SM processor 500 is described above as based upon a normalized diastolic error metric (E/A). In other embodiments, shape metrics may be based upon other pulse features such as a diastolic area, error or angle normalized by the corresponding systolic area, error or angle (Ad/As, Ed/Es, θd/θs), or shape metrics may be related to the arc length of the diastolic and/or systolic portions of a pleth pulse, to name a few. These and other pulse shapes and features responsive to respiration are also contemplated herein.

Figure 6A:
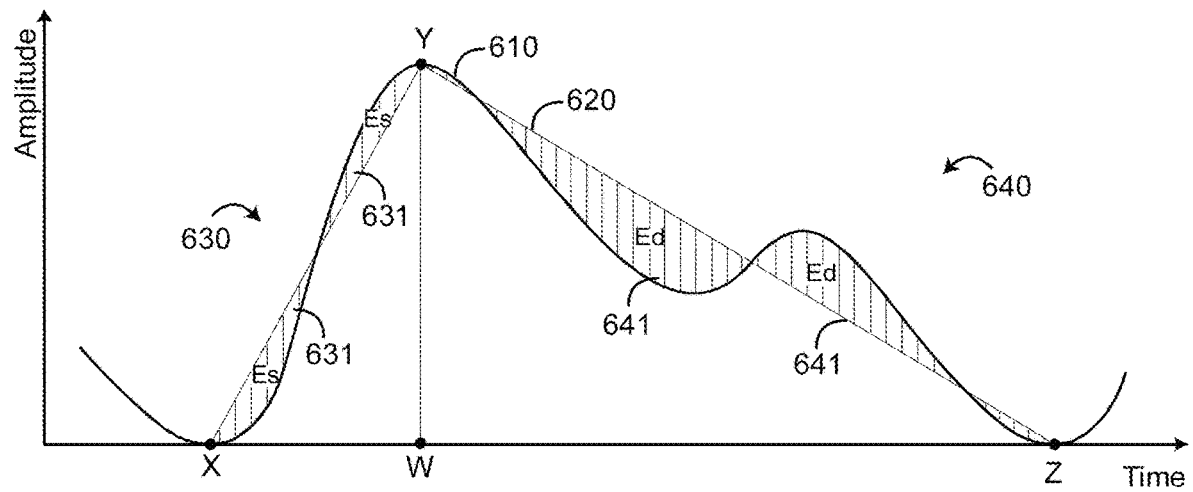
FIGS. 6A-B are intensity versus time graphs of a shape modulated pulse illustrating area-based shape metrics.
Figure 6B:
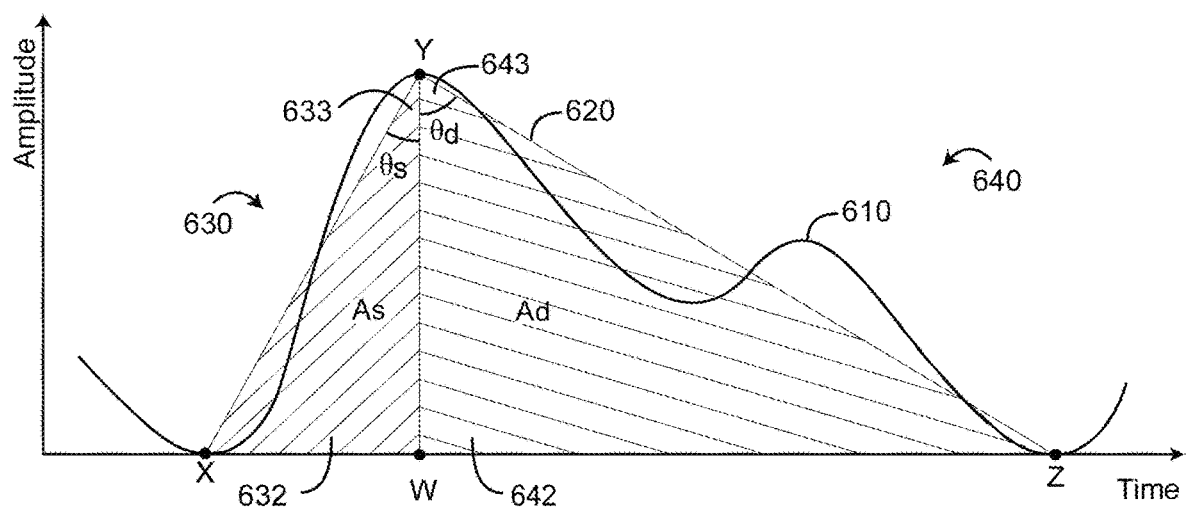

FIGS. 6A-B further illustrates pulse shape features that are derived by a feature extractor 520 (FIG. 5A) embodiment. Acceptable pleth pulses 610 are generated by the pre-processor 200 (FIG. 2A), as described above. For convenience of illustration, the inverse of an "intensity" pulse is shown, as described with respect to FIGS. 15A-B, below. The pleth pulse 610 has a peak Y at a time W and corresponding valleys at times X and Z. The peak and valleys define a triangular pulse 620 XYZ that approximates the pleth pulse 610. Further, the time line WY corresponding to the peak Y divides the pleth pulse 610 into a systolic portion 630 and a diastolic portion 640.

As shown in FIG. 6A, a systolic error Es 631 is defined as the total area between the pleth pulse 610 and the approximate triangular pulse 620 within the systolic portion 630. A diastolic error Ed 641 is defined as the total area between the pleth pulse 610 and the triangular pulse 620 within the diastolic portion 640.

As shown in FIG. 6B, a systolic area As 632 is defined as the total area under the triangular pulse 620 within the systolic portion 630. A diastolic area Ad 642 is defined as the total area under the triangular pulse 620 within the diastolic portion 640. A systolic angle θs 633 is defined as the angle XYW defined by the triangular pulse within the systolic portion 630. A diastolic angle θd 643 is defined as the angle ZYW defined by the triangular pulse within the diastolic portion 640.

Based upon the above-described pulse feature definitions, normalized pulse features may be defined. These may include normalized diastolic pulse features, such as Ed/Ad, corresponding to the diastolic triangular pulse error normalized by the diastolic triangular pulse area. Other normalized diastolic pulse features may include a diastolic area, error or angle normalized by the corresponding systolic area, error or angle (Ad/As, Ed/Es, θd/θs).

Figure 7A:
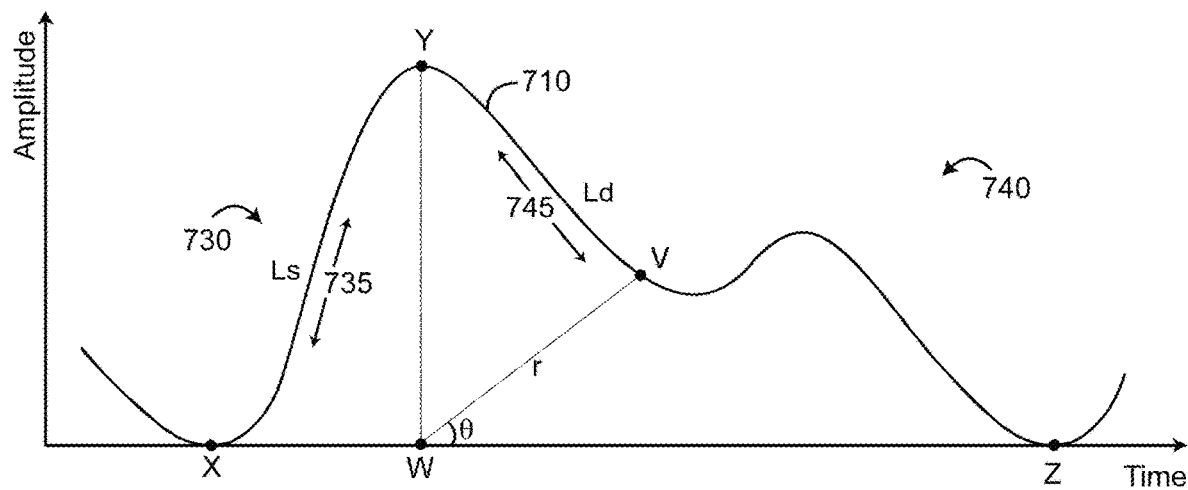
FIGS. 7A-B are intensity versus time graphs of a shape modulated pulse illustrating arc-length shape metrics.
Figure 7B:
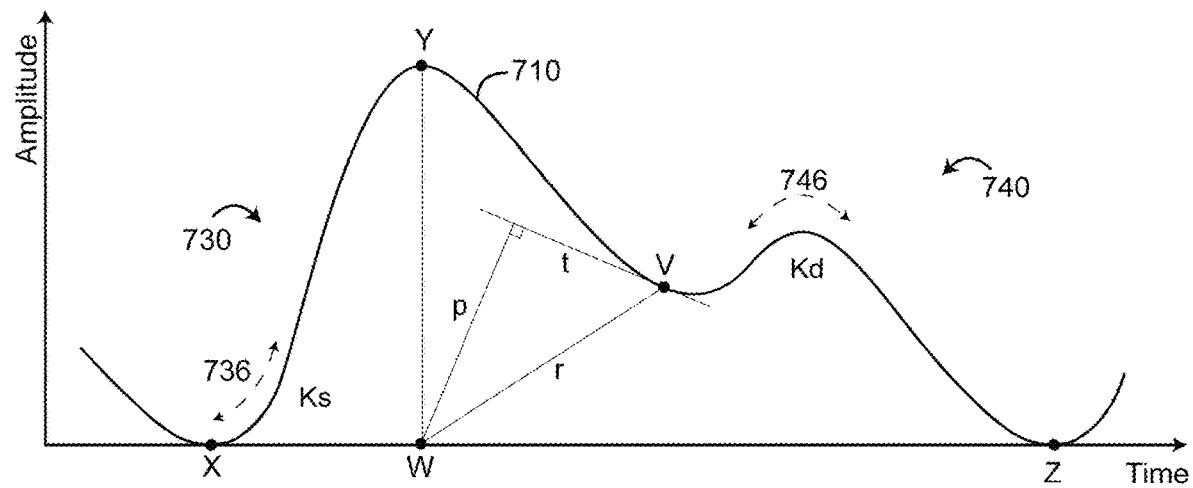

FIGS. 7A-B illustrate additional pulse shape features. As shown in FIG. 7A, pulse features may be based upon the length of a curve (trace, arc, path or line) portion of a pleth pulse 710. In particular, a diastolic curve length Ld 745 between the pulse peak Y and valley Z is defined in polar coordinates as:

$$Ld = \int_Y^Z \sqrt{r^2 + \left(\frac{dr}{d\theta}\right)^2} \, d\theta \qquad \text{(EQ. 1)}$$

where r is the distance from W (time corresponding to the peak Y) to any point V along the curve 710 and θ is the angle between r and the time axis WZ. Ld 745 may be similarly defined in Cartesian coordinates. A systolic curve length Ls 735 may be defined in similar fashion. A normalized length pulse feature Ld/Ls may be defined accordingly. In other embodiments, pulse features Ld 745 or Ls 735 may be normalized by the diastolic 640 or systolic 630 areas or angles defined with respect to FIG. 6B, above. In various embodiments, pulse features Ld 745 or Ls 735 also may be normalized by pulse height WY, by diastolic WZ or systolic XW pulse widths, by total pulse width XZ or by mathematical combinations of these measures of pulse height and pulse width to name a few.

As shown in FIG. 7B, pulse shape features may be based upon the curvature of a portion of a pleth pulse 710. In particular, a curvature Λ is defined in pedal coordinates as:

$$\kappa = \frac{1}{r}\frac{dp}{dr} \qquad \text{(EQ. 2)}$$

where the pedal coordinates of a point V with respect to the pulse 710 and the pedal point W are the radial distance r from W to V and the perpendicular distance p from W to the line t tangent to the pulse 710 at V, as shown. K may be similarly defined in Cartesian or polar coordinates. Total curvature K of a curve segment between points a and b is then $$K = \int_a^b \kappa(s)\,ds \qquad \text{(EQ. 3)}$$

A diastolic curvature Kd 746 or systolic curvature Ks 736 pulse shape feature may be defined accordingly. In other embodiments, a curvature pulse shape feature may be defined according to the absolute value of the maximum and/or minimum curvature of the pulse 710 or pulse segment 730, 740, or the curvature of a particular feature, such as a dicrotic notch. In other embodiments, pulse shape features Kd 746 or Ks 736 may be normalized by the diastolic 640 or systolic 630 areas or angles defined above with respect to FIGS. 6A-B. In various embodiments, pulse features Kd 746 or Ks 736 also may be normalized by pulse height WY, by diastolic WZ or systolic XW pulse widths, by total pulse width XZ or by mathematical combinations of these measures of pulse height and pulse width to name a few. In other embodiments, various normalized systolic and/or diastolic pulse features may be similarly defined.

FIG. 8A-D illustrate an FM processor 800 that derives an "FM" spectrum $F_{fm}$ 802 responsive to a respiration-induced frequency modulation of the pleth. As shown in FIG. 8A, the FM processor 800 has a conditioned pleth 112 input and generates a corresponding FM spectrum $F_{fm}$ 802 that is responsive to a demodulated pleth 822. In an embodiment, the demodulator 820 utilizes a metric Δ responsive to the time difference between identifiable epochs of each pleth pulse. In an embodiment, the epochs are based upon a dicrotic notch. In an embodiment, the metric Δ is the time difference between two identifiable portions of a dicrotic notch such as the notch local maximum, local minimum, or mid-point between local maximum and local minimum, to name a few.

As shown in FIG. 8B, a pleth 801 has a pleth period 871 inversely related to pulse rate (PR). Under certain conditions, an individual's respiration frequency modulates (FM) the plethysmograph 801. In particular, the modulation period 881 (FIG. 8C) is inversely related to respiration rate (RR). FIG. 8C illustrates a respiration-modulated FM metric 822 over time. In particular, an FM metric 822, such as the metric Δ described above, has a cyclical period 881 inversely related to respiration rate (RR). As shown in FIG. 8D, a spectrum 802 of the FM metric 822 includes a respiration rate (RR) peak 891.

Figure 9:
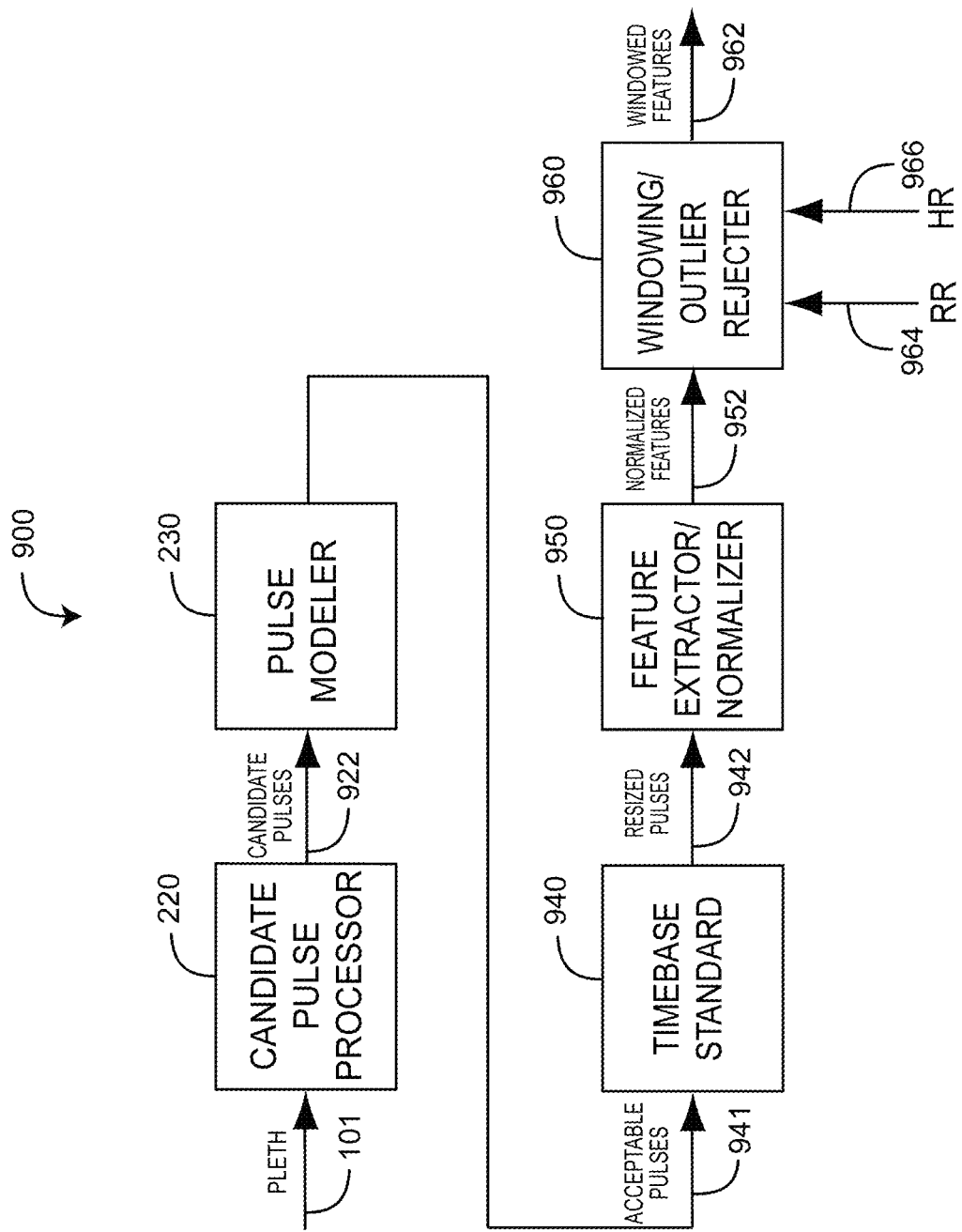
FIG. 9 is a block diagram of a pre-processor embodiment.

FIG. 9 illustrates another pre-processor 900 embodiment having a pleth 101 input and generating a windowed features 962 output. The pre-processor 900 has a candidate pulse processor 220 and pulse modeler 230 that operate on the pleth 101 input so as to generate an acceptable pulses 232 output, as described with respect to FIG. 2A, above. Further, the pre-processor 900 has a time base standard 940, a feature extractor/normalizer 950, and a windowing/outlier rejecter 960. The time base standard 940 inputs acceptable pulses 941 and outputs resized pulses 942. In particular, the time base standard 940 mathematically re-samples the input pulses 941 so that each pulse has the same number of samples. For example, if a standard pulse has 50 samples and an input pulse 941 has 60 samples, then the input pulse 941 sample interval is made larger by 60/50 or 1.2 times so that the resized input pulse width is 50 samples. Similarly, if an input pulse 941 has 40 samples, then the input pulse 941 sample interval is made smaller by 40/50 or 0.8 times so that the resized input pulse width is 50 samples. A resized input pulse is derived by interpolating the original pulse at re-sampled points. For example, a linear interpolation embodiment is used according to the following $$y = \left(\frac{y_2 - y_1}{x_2 - x_1}\right)(x - x_1) + y_1 \quad (EQ. 4)$$

where $X_2 - X_1$ is the original sample interval; $Y_1$ and $Y_2$ are input pulse 401 values at $X_1$ and $X_2$, respectively; x is a resized sample point between $X_1$ and $X_2$ and y is the resized pulse value at x. In other embodiments, the interpolation is a cubic spline or a polynomial interpolation to name a few.

Also shown in FIG. 9, the feature extractor/normalizer 950 inputs the resized pulses 942 described above and outputs normalized pulse features 952. Pulse features may include one or more of the differences or "errors" E between an acceptable pulse and its corresponding triangular pulse; areas A under the triangular pulse; and apex angles θ of a triangular pulse, to name a few, as described in detail with respect to FIGS. 6-7, above. Pulse features may also distinguish between a steeper-slope portion corresponding to systole S and a shallower-slope portion corresponding to diastole D. Pulse features are normalized by comparing one or more extracted features with one or more other extracted features. In an embodiment, normalized pulse features 952 advantageously include Ed/Ad corresponding to the diastolic triangular pulse error normalized by the diastolic triangular pulse area. Other normalized pulse features 952 may include a diastolic area, error or angle normalized by the corresponding systolic area, error or angle (Ad/As, Ed/Es, θd/θs). These and additional normalized pulse features relating to an acceptable pulse and/or its corresponding triangular pulse are also contemplated herein and described with respect to FIGS. 6-7, above.

Further shown in FIG. 9, the windowing/outlier rejecter 960 inputs the normalized features 952 and outputs windowed features 962. The windowed features 962, in turn, may be frequency transformed or analyzed in the time domain to determine a respiration modulation of the features, as described above. In particular, windowing 960 defines a sample size (window size) of the normalized features 952. The outlier rejector 960 calculates a mean or median of the normalized features 952 falling within the window, defines an acceptable range around the mean or median and rejects normalized features falling outside of that acceptable range.

Window size may be a function of a respiration rate (RR) 964, a heart rate (HR) 966 or both. In particular, HR 966 corresponds to the input pulse 101 frequency and hence determines the time between samples of the normalized features 952. RR 964 corresponds to the number of feature cycles within a window and hence sets a lower limit on the window size in order to resolve the frequency of those feature cycles.

Pulse rates may typically vary from a resting rate of 40-60 BPM for athletes to 60-90 BPM for non-athletes. Maximum heart rates are typically defined as 220—age. Hence, pulse rates might typically range from 50 to 200 BPM, which is a 4:1 variation in time between samples (0.3 sec to 1.2 sec). Respiration rates may typically vary between 12-20 breaths per minute for resting adults to 35-45 breaths per minute for exercising adults. Hence RR may typically range from 10-50 breaths per minute, which is a 5:1 variation in the number of respiration cycles per window. Accordingly, the number of pulse feature samples per respiration cycle may have a 20:1 variation.

Windowing 960 may be fixed or adjustable. Further, successive windows may be overlapping, i.e. a sliding window may be used, or may be adjacent and non-overlapping. A typical window size may range, say, between 15-120 sec. or more. Accordingly, a window size may encompass, say, 20 respiration cycles at 10 breaths per minute over a 120 sec. window to 12 respiration cycles at 50 breaths per minute over a 15 sec. window. In an embodiment, the window size is adaptively adjusted based upon detected RR and PR.

Figure 10:
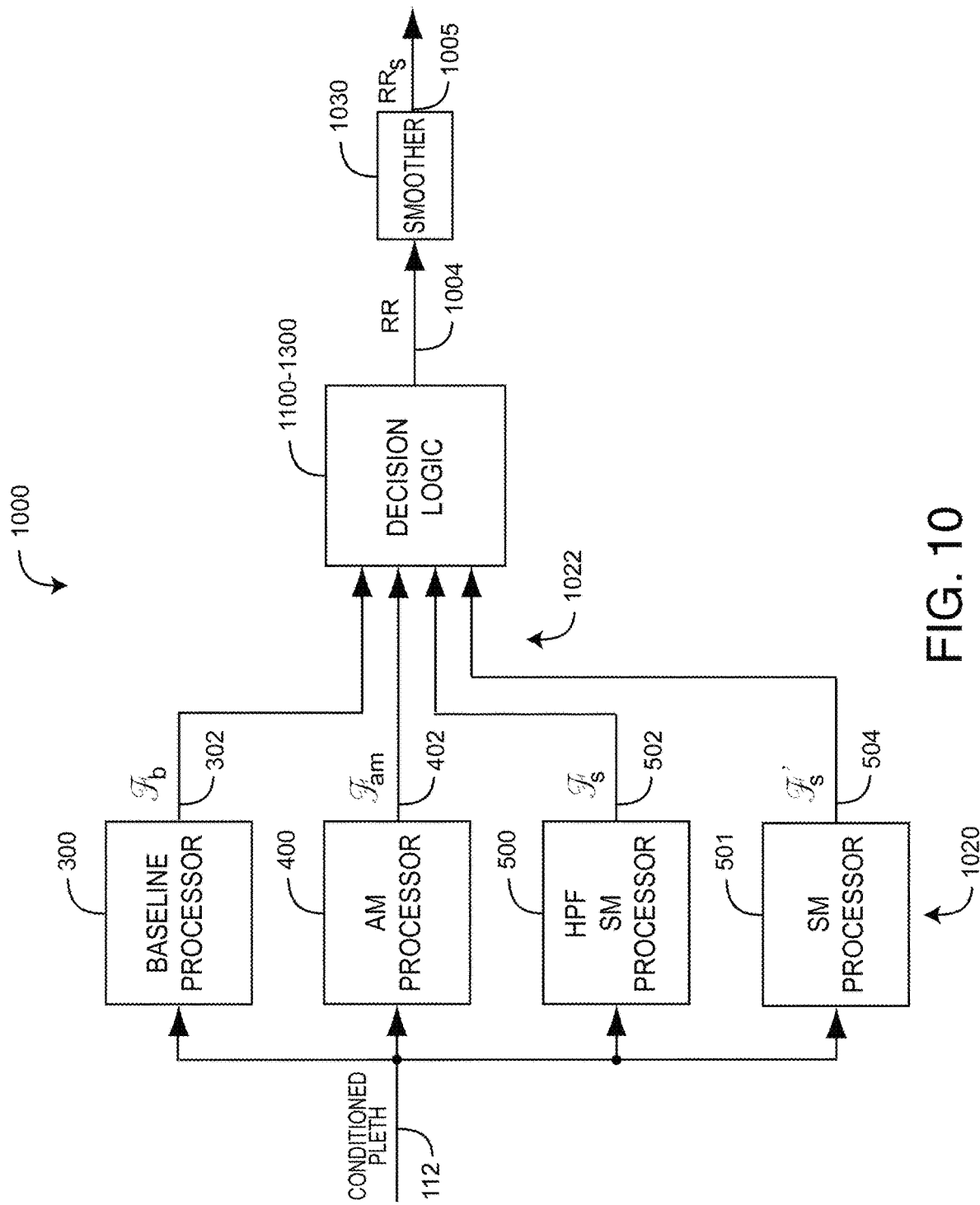
FIG. 10 is a block diagram of a plethysmographic respiration processor embodiment.

FIG. 10 illustrates a plethysmographic respiration processor 1000 embodiment having a conditioned plethysmograph waveform (pleth) 112 input and a smoothed respiration rate (RRs) 1005 output. The respiration processor 1000 includes parallel processors 1020, decision logic 1100-1300 and a smoother 1030. The conditioned pleth 112 contains pleth sections corresponding to sliding acceptable windows designated by the pre-processor 200 (FIG. 2A), as described above with respect to FIGS. 2A-B. The parallel processors 1020 each operate on conditioned pleth 112 so as to generate frequency spectrums 1022 responsive to respiration rate. The parallel processors 1020 include a baseline processor 300, an amplitude modulation (AM) processor 400, a high pass filtered (HPF) shape modulation (SM) processor 500 and a SM processor 501. In particular, the baseline processor 300 derives a "baseline" spectrum $F_b$ 302 responsive to a respiration-induced baseline shift in a pleth. The baseline processor 300 is described in detail with respect to FIGS. 3A-C, above. The AM processor 400 derives an "AM" spectrum $F_{am}$ 402 responsive to a respiration-induced amplitude modulation of the pleth. The AM processor 400 is described in detail with respect to FIGS. 4A-D, above. The SM processors 500, 501 derive "SM" spectrums $F_s$ 502, $F_s'$ 504 each responsive to a respiration-induced shape modulation of the pleth. The SM processors 500, 501 are described in detail with respect to FIGS. 5-7, above.

As described above, the processors 1020 each generate one spectrum 1022 for each sliding window of the conditioned pleth 112. Accordingly, the decision logic 1100-1300 attempts to generate a respiration rate (RR) value for each conditioned pleth 112 window. The decision logic 1100-1300 compares two or more of the spectrums $F_b$, $F_{am}$, $F_s$ and $F_s'$ 422 so as to calculate a respiration rate (RR) 1004. If the decision logic 1100-1300 cannot determine a RR 1004 value from the spectrums 1022, the corresponding conditioned pleth window 112, is rejected. A smoother 1030 generates a smoothed respiration rate 1005 calculated over multiple respiration rate 1004 values. In an embodiment, the smoother 1030 determines the median value of RR 1004 corresponding to multiple ones of the conditioned pleth windows 112. In an embodiment, the median value is calculated over five conditioned pleth windows 112. The decision logic 1100-1300 is described in detail with respect to FIGS. 11-13, below.

Figure 11A:
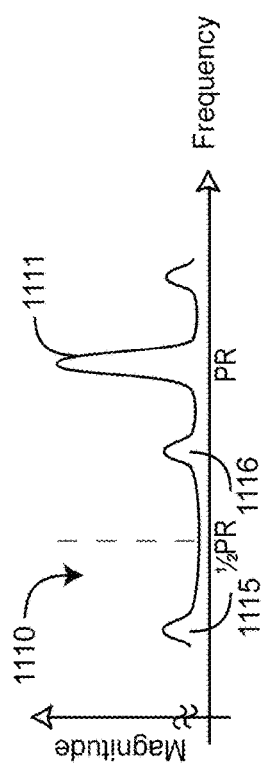
FIGS. 11A-D are a spectrums of a combined baseline shifted and AM modulated pleth; a spectrum of a demodulated baseline shifted and AM modulated pleth; a SM spectrum; and a non-idealized spectrum, respectively.
Figure 11B:
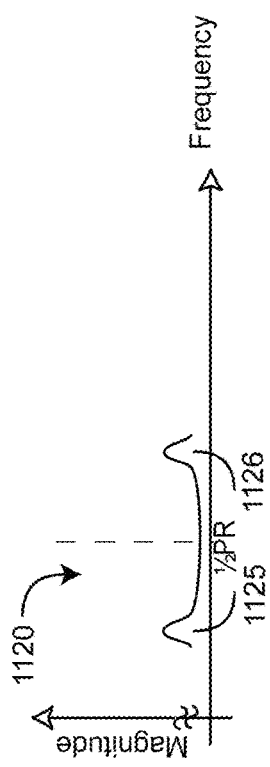
Figure 11C:
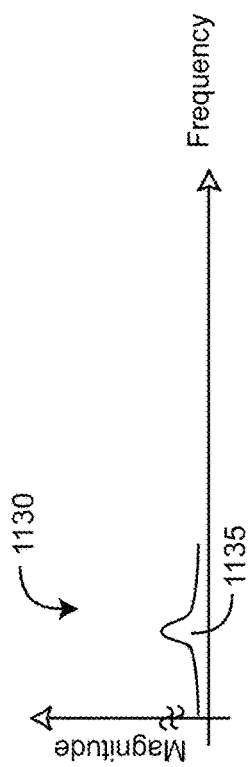

FIGS. 11A-C illustrate the output of the baseline processor 300 (FIG. 10), AM processor 400 (FIG. 10) and SM processor 500 (FIG. 10), respectively, assuming that a conditioned pleth 112 (FIG. 10) exhibits each of a baseline shift, an amplitude modulation and a shape modulation due to respiration. As shown in FIG. 11A, in view of both a respiration-induced baseline shift and AM modulation, the windowed pleth spectrum 1110 is a combination of a baseline shift spectrum 302 (FIG. 3C) and an AM spectrum 402 (FIG. 4D). This combination is also the baseline spectrum $F_b$ 302 (FIG. 3A), i.e. the frequency transform of the conditioned pleth 112. Hence, in this example, the baseline spectrum 1110 has two possible local maximums or "peaks" 1115, 1116. One peak is due to respiration shifting the pleth baseline and one peak is due to respiration amplitude modulating the pleth. However, these peaks cannot be distinguished. In particular, if RR<0.5 PR, then peak 1115 is at a frequency corresponding to RR and peak 1116 is at a frequency corresponding to PR−RR. Likewise, if RR is >0.5 PR, then peak 1115 is at a frequency corresponding to PR−RR and peak 1116 is at a frequency corresponding to RR. That is, "twin" peaks 1115, 1116 occur symmetrically on either side of frequency ½ PR, one at frequency RR and one at frequency PR-RR, but the peak corresponding to the respiration rate RR cannot be resolved by the baseline processor 302 (FIG. 10) alone.

As shown in FIG. 11B, in view of both a respiration-induced baseline shift and AM modulation, the AM spectrum $F_{am}$ 402 (FIG. 10) is a combination of the spectrums of FIG. 3C and FIG. 4C after demodulation. Hence, in this example, the AM processor output 402 (FIG. 10) has two possible local maximums or peaks 1125, 1126. One peak is due to demodulating the pleth corresponding to the spectrum of FIG. 4C, resulting in the spectrum of FIG. 4D. The other peak is due to demodulating the pleth corresponding to the spectrum of FIG. 3C, which translates the pleth fundamental 392 (FIG. 3C) at PR to DC and the respiration-related peak 391 (FIG. 3C) to PR-RR. As with the peaks described with respect to FIG. 11A, these "twin" peaks 1125, 1126 occur symmetrically on either side of ½ PR, but the peak corresponding to the respiration rate RR cannot be resolved by the AM processor 400 (FIG. 10) alone.

As shown in FIG. 11C, the SM spectrum $F_s$ 502 is unaffected by either a baseline shift or by amplitude modulation. In particular, a respiration-induced baseline shift, which shifts the entire pleth waveform up or down, has negligible effect on the error E 572 (FIG. 5B) or the triangular area A 573 (FIG. 5B). Further, although respiration-induced AM increases or decreases the pleth amplitude, this is accounted for by normalizing the error E by the triangular area A. As such, in view of both a respiration-induced baseline shift and AM, the SM spectrum $F_s$ 502 is responsive only to shape modulation, as shown in FIG. 5D, i.e. a single local maximum or peak 1135 occurs at the respiration rate.

As shown in FIGS. 11A-C, ideally respiration rate may be determined by first verifying the existence of twin peaks 1115, 1116 symmetric about 0.5 PR in the baseline spectrum 1110 and twin peaks about 0.5 PR in the AM spectrum 1120. Second, one twin from each spectrum 1110, 1120 is matched with the single peak in the SM spectrum 1130. For example, a match between peaks 1115 (FIG. 11A), 1125 (FIG. 11B) and 1135 (FIG. 11C) would provide a robust indication of RR. However, pleths from various sensors, monitors and patients may yield spectrums with erroneous peaks due to physiological conditions or artifact. Accordingly, various peaks and matching conditions are utilized by the decision logic to determine RR, as described with respect to FIGS. 12-13, below.

Figure 11D:
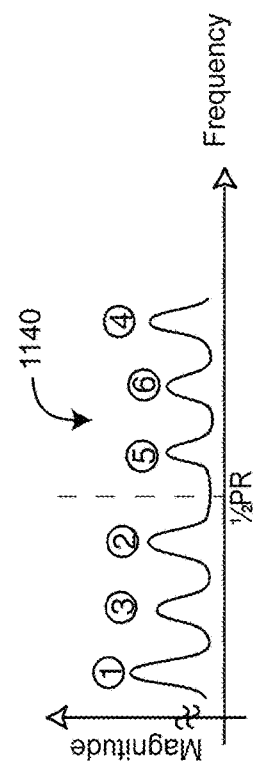

As shown in FIG. 11D, a peak identifying nomenclature 1140 is used in describing decision logic with respect to the baseline spectrum $F_b$ 302 (FIG. 10) and the AM spectrum $F_{am}$ 402 (FIG. 10). The largest peak in a spectrum is designated ① and its twin designated ④. If the largest peak is the first peak, which is sometimes erroneous, then the second largest peak is designated ② and its twin designated ⑤. If the largest peak is the last peak, which is also sometimes erroneous, the second largest peak is designated ③ and its twin designated ⑥.

Figure 12:
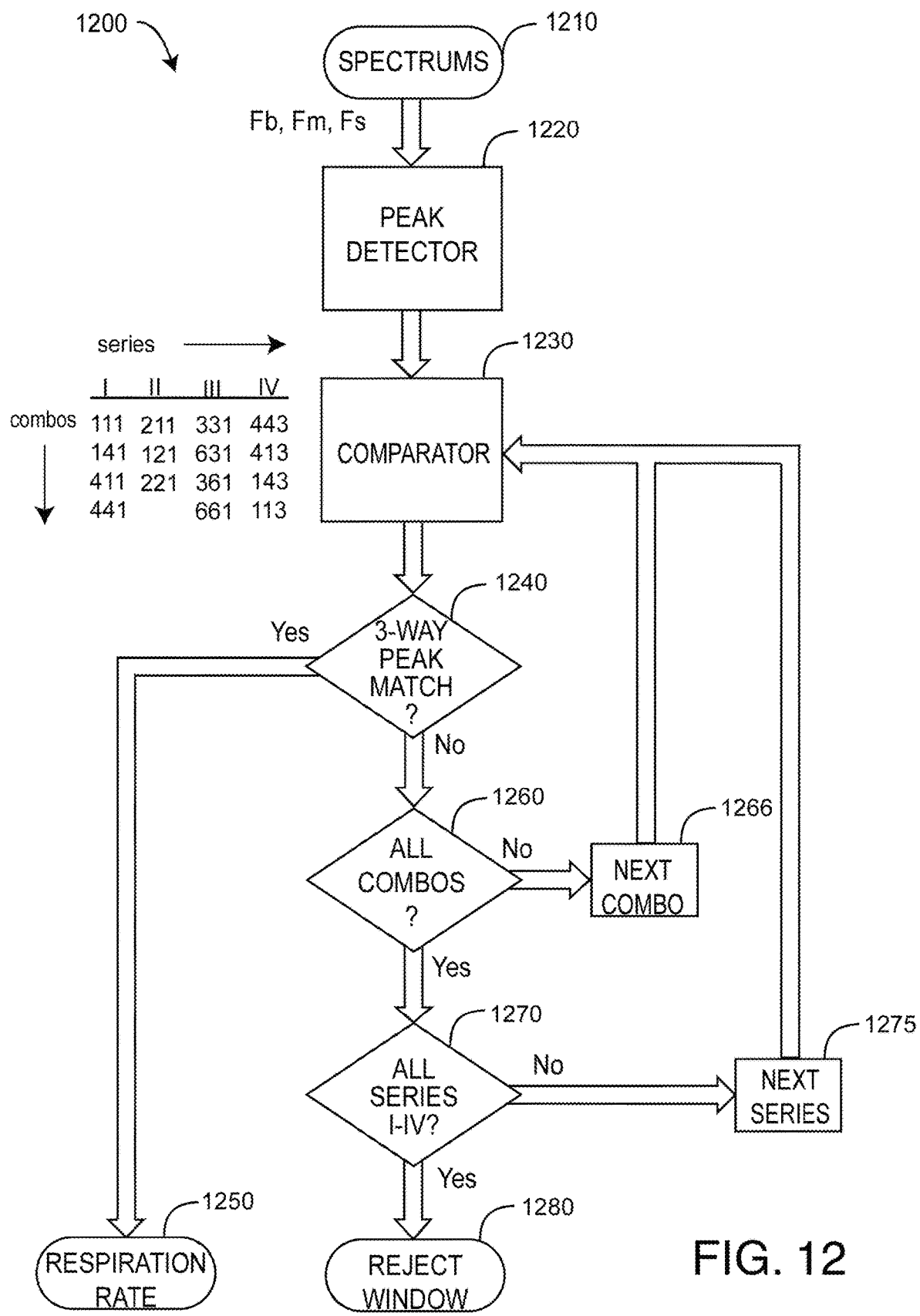
FIG. 12 is a decision logic flowchart for advantageously deriving a robust value for respiration rate based upon a baseline, an AM and a SM processor operating on an acceptable window of pleths.

FIG. 12 illustrates the decision logic 1200 for advantageously deriving a robust value for respiration rate based upon each of the baseline 300, AM 400 and SM 500 processors (FIG. 10) operating on a conditioned pleth 112 (FIG. 10). The spectrums $F_b$, $F_{am}$ and $F_s$ from these processors are input 1210 into the decision logic 1200. A peak detector 1220 locates the largest peak ① and its twin ④ from each of $F_b$ 1110 (FIG. 11A) and $F_{am}$ 1120 (FIG. 11B) and the largest peak ① from $F_s$ 1130 (FIG. 11C). The comparator 1230 looks for a three-way match from, say, the largest peak from each of the spectrums. This comparison is denoted 1-1-1, designating the largest peaks from the spectrums $F_b$-$F_{am}$-$F_s$, respectively. If the frequencies of all of these peaks match 1240, within a predetermined error, then that frequency is output as the respiration rate 1250 for that conditioned pleth window 112 (FIG. 10). If there is no match 1240, other combinations 1260, 1266 of peaks of a particular series are compared 1230, such as the largest peak from $F_b$, the twin to the largest peak from $F_{am}$ and the largest peak from $F_s$, denoted 1-4-1. Hence, all of the following combinations are denoted the first series of combinations to try, i.e. series I: 1-1-1; 1-4-1; 4-1-1; 4-4-1.

As shown in FIG. 12, if there are no matches from series I, other series 1270, 1275 having different types of combinations are tried, as explained below. If a particular twin cannot be located, the corresponding series is rejected 1275. If no 3-way matching peaks are found after trying all combinations in each of series I, II, III, IV 1270, then that particular window is rejected 1280 and no respiration rate value is determined that corresponds to that window.

Series II represents a second set of peak comparisons. In some cases, the largest peak ① from $F_b$ or $F_{am}$ or both may be the first peak, which is often erroneous. As such, comparisons may be made using the second largest peaks ② from $F_b$ and $F_{am}$ and the corresponding twins ⑤. The twins in this series are verified to exist, but not used. Accordingly, in an embodiment, the largest peaks ① and the second largest peaks ② are compared in the following combinations: 2-1-1; 1-2-1; 2-2-1.

Series III represents a third set of peak comparisons. In some cases, the largest peak from $F_b$ or $F_{am}$ or both may be the last peak, which is also often erroneous. As such, comparisons may be made using the second largest peaks ③ from $F_b$ and $F_{am}$ and the corresponding twins ⑥. Accordingly, in an embodiment, these peaks are compared in the following combinations: 3-3-1; 6-3-1; 3-6-1; 6-6-1.

Series IV represents yet another set of peak comparisons. In some cases, the largest peak from $F_s$ is erroneous. Hence, comparisons may be made using the largest peak from $F_s'$, designated ③, and the largest peak and corresponding twin from $F_b$ and $F_{am}$, designated ① and ④, as noted above. Accordingly, in an embodiment, these peaks are compared with each other in the following combinations: 4-4-3; 4-1-3; 1-4-3; 1-1-3. In other embodiments, other combinations are possible, for example, the twins to the second largest peaks from $F_b$ and $F_{am}$, which are designated ⑤, could be used in various combinations with other designated peaks described above. If all combinations fail to yield a three-way match 1240, then that particular window is rejected 1280.

Figure 13:
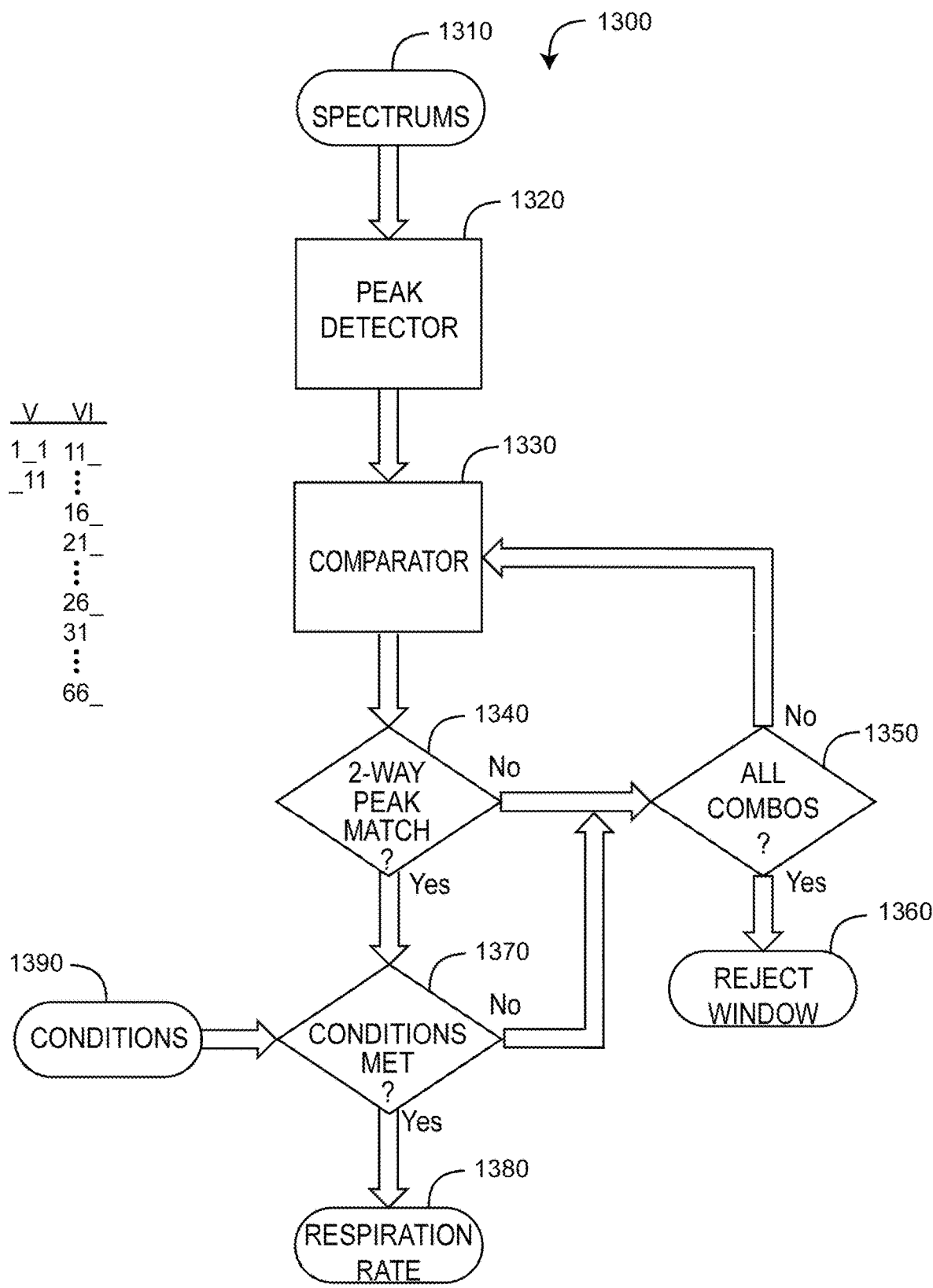
FIG. 13 is a decision logic flowchart for advantageously deriving a robust value for respiration rate based upon a baseline, an AM and a high pass filtered (HPF) SM processor operating on an acceptable window of pleths.

FIG. 13 illustrates decision logic 1300 for advantageously deriving a robust value for respiration rate based upon a two-way match of the spectrums $F_b$, $F_{am}$ and $F_s$ (or $F_s'$) from each of the baseline 300, AM 400 and shape 500, 501 processors (FIG. 10) plus an additional condition 1390. In an embodiment, decision logic 1300 is used in the event a respiration rate RR 1004 (FIG. 10) cannot be derived from a three-way match of the spectrums $F_b$, $F_{am}$ and $F_s$ (or $F_s'$), as described with respect to FIG. 12, above.

As shown in FIG. 13, in a series V, the largest peaks from $F_b$ and $F_s$, denoted 1_1 (without utilizing $F_{am}$) are compared for a two-way match 1330. If there is a match, an additional condition 1370 must be met. In an embodiment, the condition 1390 is that the matching frequencies of $F_b$ and $F_s$ must be within a predetermined difference of the smoothed respiration rate (RRs) 1005 (FIG. 10). In an embodiment, the predetermined difference is 1 bpm. If so, the matching frequencies are output as the respiration rate RR 1380. If not, the largest peaks from $F_{am}$ and $F_s$, denoted _11 (without utilizing $F_b$) are also compared for a match 1330. If there is a match from this comparison and the additional condition 1370 is met, then the matching frequencies are output as the respiration rate RR 1380. If these combinations are compared without a match 1350, then a series VI is utilized.

Also shown in FIG. 13, in a series VI, the various peaks from $F_b$ and $F_{am}$, each denote 1-6, are compared for a two-way match 1330. If there is a match, the additional condition 1370 must be met. If all combinations, e.g. 11, 12, 13 . . . 21, 22, 23 . . . 36, 46, 56 are tried without a match or there is a match but the additional condition is not met, the window is rejected 1360. In other embodiments, other peaks are compared 1330 and other conditions 1390 must be met.

Figure 14:
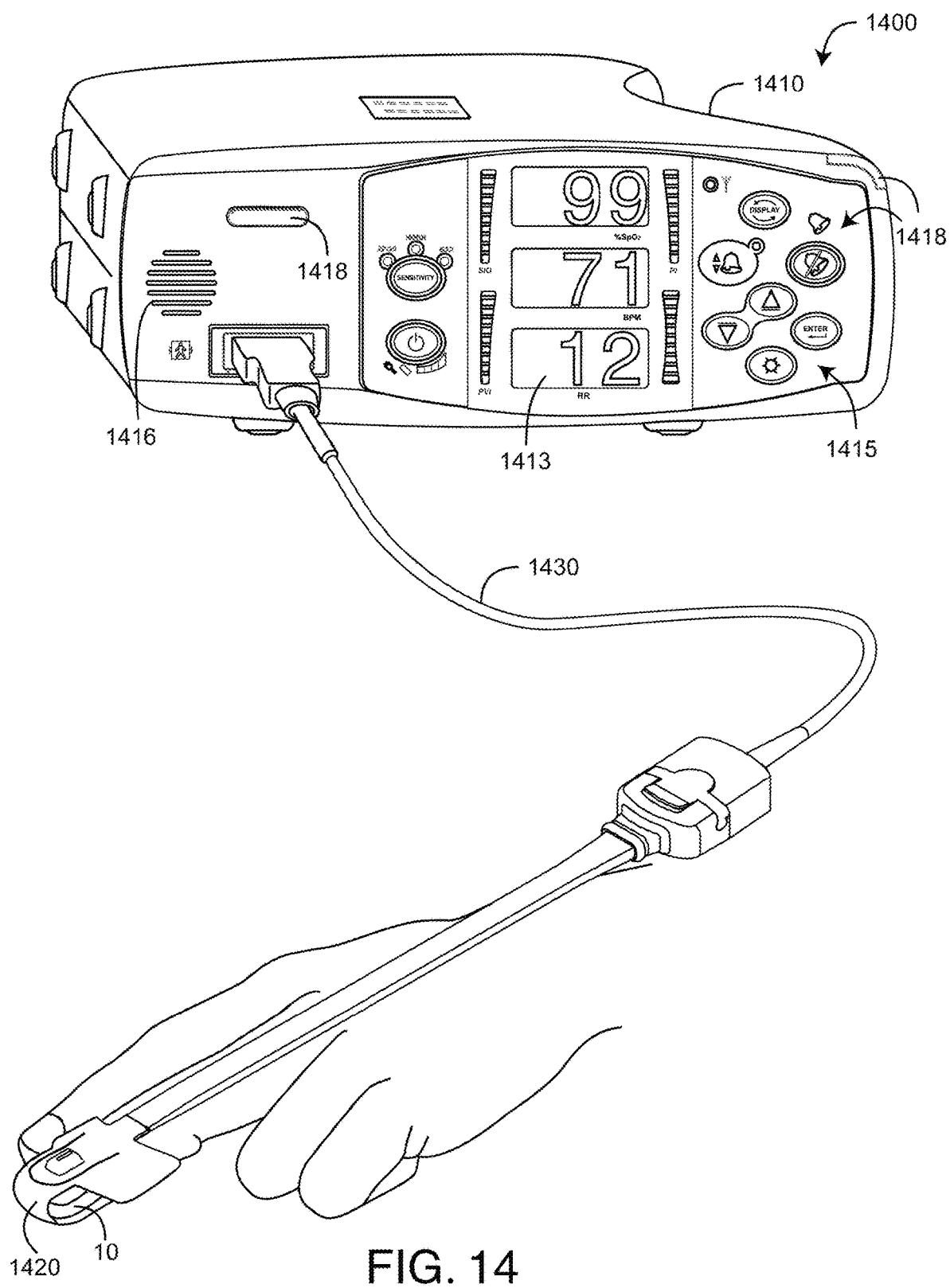
FIG. 14 is a perspective view of a non-invasive physiological parameter measurement system having a monitor and a corresponding optical sensor and incorporating a plethysmographic respiration processor.

FIG. 14 illustrates a physiological monitoring system 1400 that incorporates a plethysmographic respiration processor 100 (FIG. 1), as described above. The monitoring system 1400 has a monitor 1410, an optical sensor 1420 and an interconnect cable 1430 connecting the monitor 1410 and sensor 1420. The monitoring system 1400 generates physiological parameters that indicate one or more aspects of a person's physical condition, including, advantageously, a plethysmograph-derived respiration rate. The sensor 1420 attaches to a tissue site 10, such as a fingertip, and is capable of irradiating the tissue site 10 with differing wavelengths of light and detecting the light after attenuation by pulsatile blood flow within the tissue site 10. The monitor 1410 communicates with the sensor 1420 via the interconnect cable 1430 to receive one or more detected intensity signals and to derive from those intensity signals one or more physiological parameters. The monitor also has a display 1413 for presenting parameter values, including respiration rate (RR). Controls 1415 set alarm limits, processing modes, display formats and more. An audio transducer 1416 provides alarm sounds, pulse beeps and button press feedback to name a few. Indicators 1418 show monitor status. The display 1413 may include readouts, colored lights or graphics generated by LEOs, LCOs or CRTs to name a few and is capable of displaying indicia representative of calculated physiological parameters, including respiration rate, and waveforms, including plethysmographs. The display 1413 is also capable of showing historical or trending data related to one or more of the measured parameters or combinations of the measured parameters. User I/O may include, for example, push buttons 1415 and indicators 1418. The push buttons may be soft keys with display-indicated functions or dedicated function keys 1415. Other user I/O (not shown) may include keypads, touch screens, pointing devices, voice recognition devices and the like.

Figure 15A:
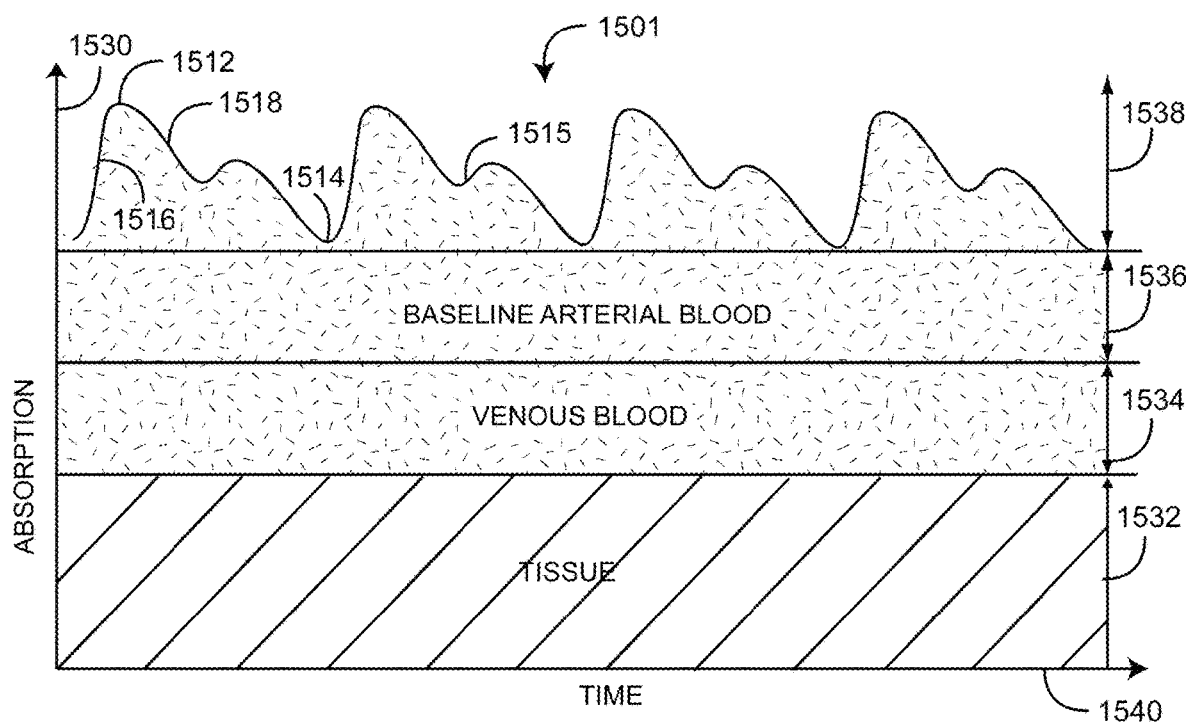
FIGS. 15A-B are graphs of light absorption profiles for pulsatile blood perfused tissue and surrounding tissue and an optical sensor detected light intensity, respectively.

FIG. 15A illustrates a light absorption waveform 1501 at an illuminated peripheral tissue site corresponding to a pulsatile blood volume at that site. The peripheral tissue site is illuminated by, and the corresponding absorption is (indirectly) measured by, an optical sensor 1420 (FIG. 14), as described above. A y-axis 1530 represents the total amount of light absorbed by the tissue site, with time shown along an x-axis 1540. The total absorption is represented by layers, including the static absorption layers due to tissue 1532, venous blood 1534 and a baseline of arterial blood 1536. Also shown is a variable absorption layer 1538 due to the pulse-added volume of arterial blood that is used to derive a plethysmograph, as described above and further with respect to FIG. 15B, below. This light absorption waveform 1501 varies as a function of the wavelength of the optical sensor emitted light according to the blood constituency. Indeed, it is this wavelength variation that allows a multiparameter patient monitor to determine blood hemoglobin components and other blood constituents along with respiration rate characteristics, as described above.

As shown in FIG. 15A, a pulsatile blood volume 1538 is a function of heart stroke volume, pressure gradient, arterial elasticity and peripheral resistance. The ideal pulsatile blood volume waveform displays a broad peripheral flow curve, with a short, steep inflow phase 1516 followed by a 3 to 4 times longer outflow phase 1518. The inflow phase 1516 is the result of tissue distention by the rapid blood volume inflow during ventricular systole. During the outflow phase 1518, blood flow continues into the vascular bed during diastole. The end diastolic baseline 1514 indicates the minimum basal tissue perfusion. During the outflow phase 1518 is a dicrotic notch 1515. Classically, the dicrotic notch 1515 is attributed to closure of the aortic valve at the end of ventricular systole. However, it is also a function of reflection from the periphery of an initial, fast propagating pressure pulse that occurs upon the opening of the aortic valve preceding the arterial flow wave. Pulsatile blood volume varies with physiological properties such as heart stroke, vessel size, elasticity and vascularization, to name a few. Accordingly, the blood flow waveform shape can vary significantly from individual to individual and between tissue sites.

Figure 15B:
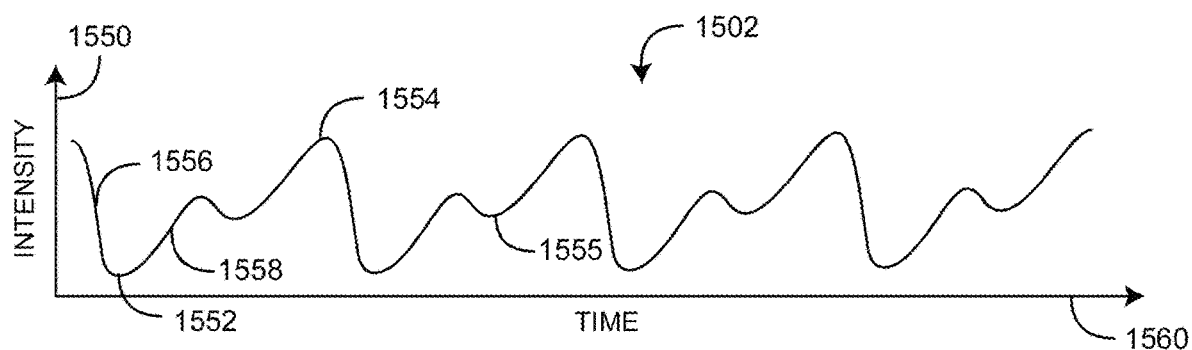

FIG. 15B illustrates a plethysmograph waveform 1502 detected by an optical sensor 1420 (FIG. 14). In particular, detected intensity is shown along the y-axis 1550 versus time shown along the x-axis 1560. The plethysmograph waveform 1502 is a time series of plethysmograph ("pleth") pulses and relates to the time-varying pulsatile blood volume 1538 (FIG. 15A) measured at a particular location on a person, referred to herein as a "tissue site." A tissue site can be a fingertip, ear lobe, toe, nose or forehead to name just as few. A person is used herein as the referenced subject of optical sensor measurements, but other living species also have a measurable pleth and are included within the scope of this disclosure.

As shown in FIG. 15B, an optical sensor 1420 (FIG. 14) does not directly detect absorption and, hence, does not directly measure the volume waveform 1538 (FIG. 15A). However, the plethysmograph waveform 1502 is merely an out-of-phase version of the volume profile 1538. Stated differently, the plethysmograph waveform 1502 varies inversely with the pulsatile blood volume 1538. In particular, the peak detected intensity 1554 occurs at minimum volume 1514 and the minimum detected intensity 1552 occurs at maximum volume 1512. Further, a rapid rise in volume during the inflow phase 1516 is reflected in a rapid decline in intensity 1556; and the gradual decline in volume during the outflow phase 1518 is reflected in a gradual increase 1558 in detected intensity. The intensity waveform 1502 also displays a dicrotic notch 1555.

Figure 16:
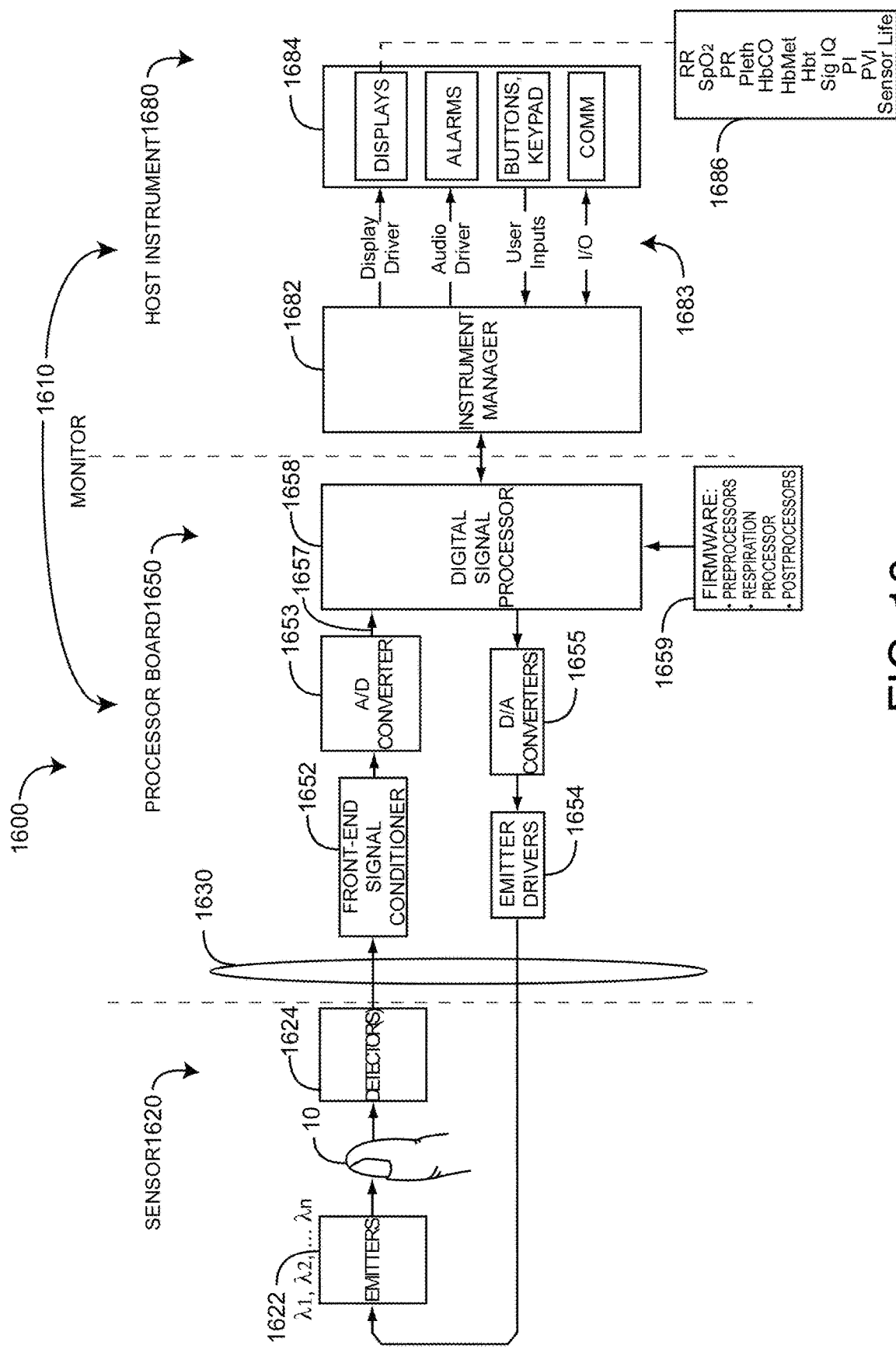
FIG. 16 is block diagram of a non-invasive physiological parameter measurement system having a monitor and a corresponding optical sensor and incorporating a plethysmographic respiration processor.

FIG. 16 further illustrates a physiological monitoring system 1600 having an optical sensor 1620 attached to a tissue site 10, a monitor 1610 and an interconnecting sensor cable 1620. The sensor 1620 has emitters 1622, each of which transmit light of a specified wavelength. Drivers 1654, 1655 convert digital control signals into analog drive signals capable of activating the emitters 1622. A front-end 1652, 1653 converts composite analog intensity signal(s) from the detector(s) 1624 into digital data input to a digital signal processor (DSP) 1658. The DSP 1658 may comprise any of a wide variety of data and/or signal processors capable of executing programs for determining physiological parameters from input data. In an embodiment, the DSP executes firmware 1659 including pre-processors, respiration processors and post processors, such as described with respect to FIGS. 1-13, above.

Also shown in FIG. 16, an instrument manager 1682 may comprise one or more microcontrollers controlling system management, such as monitoring the activity of the DSP 1658. The instrument manager 1682 has an interface port 1683 for monitor communications. In an embodiment, the interface port 1683 has a display driver, an audio driver, user inputs and I/O for driving displays and alarms, responding to buttons and keypads and providing external device input/output communications. In an embodiment, the displays can indicate a variety of physiological parameters 1686 such as respiration rate (RR), pulse rate (PR), plethysmograph (pleth), perfusion index (PI), pleth variability index (PVI), signal quality (IQ) and values for blood constituents including oxygen saturation ($SpO_2$), carboxyhemoglobin (HbCO), methemoglobin (HbMet), total hemoglobin (Hbt) and oxygen content (OC) as well as instrument and sensor status, such as sensor life, to name but a few.

FIG. 17 illustrates a demodulator 1700 having a modulated/multiplexed detector signal 1703 input and demodulated signal 1705 outputs. That is, the demodulator input 1703 is the result of a detector 1624 (FIG. 16) response to N emitter wavelengths 1622 (FIG. 16) that are cyclically turned on and off by emitter drivers 1654 (FIG. 16) so as to illuminate a tissue site with multiple wavelength optical radiation, as is well known in the pulse oximetry art. The digitized detector signal 1703 corresponds to the A/D converter 1657 (FIG. 16) input to the DSP 1658 (FIG. 16). The DSP has demodulator 1700 (preprocessor) firmware 1659 which generates N channels of demodulated signals $r_1(t)$, $r_2(t)$, . . . , $r_N(t)$ 1705 in response. One signal $r_i(t)$ corresponding to each emitter wavelength 1622. These demodulated signals are plethysmographs, as described above.

The demodulator 1700 has mixers 1730 and low pass filters 1740 for each channel and demodulating signals $d_i(t)$ 1704 provided to each mixer 1730. The demodulating signals are linear combinations of (orthogonal) basis functions of the form $$d_i(t) = \sum_{j=1}^{M} \beta_{ij} \cdot \phi_j(t) \qquad (EQ. 5)$$

which are derived by approximating the optical response of the emitters to on/off periods of the emitter drivers. M is the number of basis functions needed to approximate such optical responses. $\phi_j(t)$ is the $j^{th}$ basis function used by the demodulator. In one embodiment, the basis functions are of the form $$\phi_j(t) = \sin\left(\frac{2\pi}{T} jt + b_j \frac{\pi}{2}\right); b_j \in [0, 1] \qquad (EQ. 6)$$

where T is the period of the repeating on/off patterns of the emitter drivers. Accordingly, the lowpass filter outputs 1705 are $r_1(t), r_2(t), \ldots, r_N(t)$, which are estimates of absorption for each emitter wavelength in view of noise n(t) that is additive to each channel. Plethysmograph demodulators are described in U.S. Pat. No. 5,919,134 titled Method and Apparatus for Demodulating Signals in a Pulse Oximetry System, issued Jul. 6, 1999; U.S. Pat. No. 7,003,338 titled Method and Apparatus for Reducing Coupling Between Signals, issued Feb. 21, 2006; and U.S. patent application Ser. No. 13/037,321 titled Plethysmograph Filter, filed Feb. 28, 2011; all assigned to Masimo Corporation and incorporated by reference herein.

Advantageously, a plethysmographic respiration processor 100 (FIG. 1) is implemented on an advanced pulse oximetry monitor or an advanced blood parameter monitor, as described above. Although a plethysmographic respiration processor is described above with respect to deriving respiration rate from a plethysmograph waveform, in other embodiments, a plethysmographic respiration processor may be used to derive other respiration-related parameters. In a particularly advantageous embodiment, a plethysmographic respiration processor is used in conjunction with an acoustic monitor or combined blood parameter and acoustic monitor so as to improve the accuracy of, robustness of, or otherwise supplement acoustic-derived respiration rate measurements or other acoustic-derived respiration parameters.

A plethysmographic respiration processor has been disclosed in detail in connection with various embodiments. These embodiments are disclosed by way of examples only and are not to limit the scope of the claims herein. One of ordinary skill in art will appreciate many variations and modifications.

What is claimed is:

1. A patient monitor configured to determine a respiration rate from a plethysmograph waveform, the patient monitor comprising:
    a preprocessor configured to receive a plethysmograph waveform from a noninvasive sensor monitoring a patient and identify a plurality of portions of the plethysmograph waveform which include physiologically acceptable series of plethysmograph waveform pulses; and
    one or more processors configured to:
        derive a first set of frequencies from a first respiratory-induced modulation in a portion of the plurality of portions,
        derive a second set of frequencies from a second respiratory-induced modulation in the portion, the second respiratory-induced modulation being different from the first respiratory-induced modulation,
        compare the first set of frequencies and the second set of frequencies to determine whether any of the first set of frequencies matches any of the second set of frequencies within a tolerance,
        generate and output a respiration rate in real time to a display from determining that one of the first set of frequencies matches one of the second set of frequencies within the tolerance, and
        activate an alarm in real time if the respiration rate satisfies an alarm threshold.

2. The patient monitor of claim 1, wherein the one or more processors is configured to compare the first set of frequencies and the second set of frequencies until at least determining that none of at least two of the first set of frequencies match none of at least two of the second set of frequencies within the tolerance.

3. The patient monitor of claim 1, wherein the one or more processors is configured to compare the first set of frequencies and the second set of frequencies by comparing individual frequencies of the first set of frequencies and individual frequencies of the second set of frequencies in an order that depends on a pulse rate for the patient.

4. The patient monitor of claim 1, wherein the one or more processors is configured to:
    derive a third set of frequencies from a third respiratory-induced modulation in the portion, the third respiratory-induced modulation being different from the first respiratory-induced modulation and the second respiratory-induced modulation;
    compare the first set of frequencies, the second set of frequencies, and the third set of frequencies to determine whether any of the first set of frequencies matches any of the second set of frequencies and any of the third set of frequencies within the tolerance; and
    generate and output the respiration rate in real time to the display from determining that the one of the first set of frequencies matches the one of the second set of frequencies and one of the third set of frequencies within the tolerance.

5. The patient monitor of claim 1, wherein the portion comprises plethysmograph data captured from monitoring the patient over a period less than 120 seconds.

6. The patient monitor of claim 1, wherein the one or more processors is configured to:
    derive a third set of frequencies from the first respiratory-induced modulation in another portion of the plurality of portions;
    derive a fourth set of frequencies from the second respiratory-induced modulation in the another portion;
    compare the third set of frequencies and the fourth set of frequencies to determine whether any of the third set of frequencies matches any of the fourth set of frequencies within the tolerance;
    generate another respiration rate from determining that one of the third set of frequencies matches one of the fourth set of frequencies within the tolerance; and
    derive a combined respiration rate from the respiratory rate and the another respiratory rate.

7. The patient monitor of claim 6, wherein the one or more processors is configured to:
    derive a fifth set of frequencies from the first respiratory-induced modulation in yet another portion of the plurality of portions;
    derive a sixth set of frequencies from the second respiratory-induced modulation in the yet another portion;
    compare the fifth set of frequencies and the sixth set of frequencies to determine whether any of the fifth set of frequencies matches any of the sixth set of frequencies within the tolerance;
    generate yet another respiration rate from determining that one of the fifth set of frequencies matches one of the sixth set of frequencies within the tolerance;
    determine that the yet another respiration rate differs from the combined respiration rate by more than an amount; and
    reject the yet another respiration rate in response to determining that the yet another respiration rate differs from the combined respiration rate by more than the amount.

8. The patient monitor of claim 6, wherein the portion comprises plethysmograph data captured from monitoring the patient over a different period than the another portion.

9. The patient monitor of claim 1, wherein the one or more processors is configured to generate and output the respiration rate in real time to the display from determining that the one of the first set of frequencies matches the one of the second set of frequencies within the tolerance and from determining that an additional condition is met.

10. The patient monitor of claim 9, wherein the additional condition is met when the respiration rate differs from a value by less than an amount.

11. The patient monitor of claim 1, wherein the first respiratory-induced modulation comprises a respiratory-induced baseline shift of the portion, and the second respiratory-induced modulation comprises a respiratory-induced amplitude modulation of the portion.

12. The patient monitor of claim 1, wherein the first respiratory-induced modulation comprises a respiratory-induced baseline shift of the portion, and the second respiratory-induced modulation comprises a respiratory-induced shape modulation of the portion.

13. The patient monitor of claim 1, wherein the first respiratory-induced modulation comprises a respiratory-induced amplitude modulation of the portion, and the second respiratory-induced modulation comprises a respiratory-induced shape modulation of the portion.

14. The patient monitor of claim 1, further comprising the display configured to present the respiration rate.

15. The patient monitor of claim 1, wherein the respiration rate comprises the one of the first set of frequencies.

16. The patient monitor of claim 1, further comprising the noninvasive sensor.

* * * * *